United States Patent
Payton et al.

(10) Patent No.: US 9,925,348 B2
(45) Date of Patent: Mar. 27, 2018

(54) GAS DELIVERY DEVICE

(71) Applicant: UPODS, LLC, Lehigh, PA (US)

(72) Inventors: Hugh W. Payton, Black Mountain, NC (US); Campbell C. Cauthen, Black Mountain, NC (US); John Stephens, Alpharetta, GA (US)

(73) Assignee: UPODS, LLC, Lehigh Valley, PA (US)

( * ) Notice: Subject to any disclaimer, the term of this patent is extended or adjusted under 35 U.S.C. 154(b) by 0 days.

(21) Appl. No.: 15/235,665

(22) Filed: Aug. 12, 2016

(65) Prior Publication Data

US 2016/0346495 A1 Dec. 1, 2016

Related U.S. Application Data

(63) Continuation-in-part of application No. 14/599,228, filed on Jan. 16, 2015, now Pat. No. 9,440,039, which
(Continued)

(51) Int. Cl.
*A61M 16/06* (2006.01)
*A61M 25/02* (2006.01)
*A61M 16/10* (2006.01)

(52) U.S. Cl.
CPC .... *A61M 16/0672* (2014.02); *A61M 16/0683* (2013.01); *A61M 16/0688* (2014.02);
(Continued)

(58) Field of Classification Search
CPC .......... A61M 16/0666; A61M 16/0672; A61M 16/0677; A61M 16/0688; A61M 16/0683;
(Continued)

(56) References Cited

U.S. PATENT DOCUMENTS 419,942 A 1/1890 Harding et al.
1,873,160 A * 8/1932 Sturtevant ............. A61M 16/00
128/206.11
(Continued)

FOREIGN PATENT DOCUMENTS

WO 199220392 11/1992
WO 2005014080 2/2005
WO 2013168134 11/2013

OTHER PUBLICATIONS

ATC Medical, Nasal Cannula Adult with 7ft. Tubing, located at http://www.atcmedical.com/Respiratory/Cpap-Bipap-SuppliesNVestmed_Comfort_Soft_Pl . . . , printed Jan. 12, 2016, 1 page.
(Continued)

*Primary Examiner* — Valerie L Woodward
(74) *Attorney, Agent, or Firm* — David W. Carstens; Shaukat A. Karjeker; Carstens & Cahoon, LLP

(57) ABSTRACT

A system for delivery of a gas to a user has a single tubular nasal cavity component having only two terminal ends: a gas inlet and a gas outlet with a single gas flow path between. The component is configured for insertion into the nostril of a user and maintains the position without adhesive. The nasal cavity component includes a first portion having a first longitudinal axis along the single gas flow path. A proximal end of the first portion is flared outward for insertion into a nostril of a patient. A second portion has a second longitudinal axis, and a gas inlet end to receive gas from a gas supply. A distal end of the second portion intersects a distal end of the first portion in a bend portion, such that the first and second longitudinal axes intersect at an angle of between about 60 and about 80°.

27 Claims, 13 Drawing Sheets

Related U.S. Application Data is a continuation-in-part of application No. 13/944,226, filed on Jul. 17, 2013.

(52) U.S. Cl.
CPC ............... A61M 2016/102 (2013.01); A61M 2025/0226 (2013.01); A61M 2025/0266 (2013.01); A61M 2202/0208 (2013.01); A61M 2205/0266 (2013.01); A61M 2205/3569 (2013.01); A61M 2205/3592 (2013.01); A61M 2206/16 (2013.01); A61M 2209/088 (2013.01)

(58) Field of Classification Search
CPC ............... A61M 15/08; A61M 15/085; A61M 2025/0226; A61M 2025/024; A61M 2025/0253; A61M 2025/026; A61F 5/08; A62B 23/06
See application file for complete search history.

(56) References Cited

U.S. PATENT DOCUMENTS

| | | | | |
|---|---|---|---|---|
| 2,168,705 | A | 10/1939 | Francisco et al. | |
| 3,400,714 | A | 10/1968 | Sheridan | |
| 3,802,431 | A | 4/1974 | Farr | |
| 4,273,124 | A | 6/1981 | Zimmerman | |
| 4,278,072 | A | 7/1981 | Blackmer | |
| 4,648,398 | A | 3/1987 | Agdanowski et al. | |
| 4,660,555 | A * | 4/1987 | Payton | A61M 16/0488 128/207.18 |
| 4,685,456 | A | 8/1987 | Smart | |
| 4,708,446 | A | 11/1987 | Timmons et al. | |
| 4,736,741 | A | 4/1988 | Payton et al. | |
| 4,742,824 | A * | 5/1988 | Payton | A61M 16/0666 128/207.18 |
| 5,193,534 | A | 3/1993 | Peppler | |
| 5,477,852 | A | 12/1995 | Landis et al. | |
| 5,533,506 | A | 7/1996 | Wood | |
| 5,595,174 | A | 1/1997 | Gwaltney | |
| 6,439,234 | B1 | 8/2002 | Curti et al. | |
| 6,533,983 | B2 | 3/2003 | Curti | |
| 6,533,984 | B2 | 3/2003 | Curti | |
| 6,551,285 | B1 | 4/2003 | Bierman | |
| 6,684,883 | B1 | 2/2004 | Burns | |
| 6,772,761 | B1 * | 8/2004 | Rucker, Jr. | A61M 16/0666 128/207.14 |
| 6,804,866 | B2 | 10/2004 | Lemke et al. | |
| 6,807,966 | B2 | 10/2004 | Wright | |
| 6,913,017 | B2 | 7/2005 | Roberts | |
| 7,337,780 | B2 | 3/2008 | Curti et al. | |
| 7,364,682 | B2 | 4/2008 | Curti et al. | |
| 7,565,907 | B2 | 7/2009 | Curti et al. | |
| 7,743,770 | B2 | 6/2010 | Curti et al. | |
| 7,832,400 | B2 | 11/2010 | Curti et al. | |
| D643,113 | S | 8/2011 | Butler | |
| 8,136,527 | B2 | 3/2012 | Wondka | |
| 8,161,971 | B2 | 4/2012 | Jaffe et al. | |
| 8,161,972 | B2 | 4/2012 | Jaffe et al. | |
| 8,225,796 | B2 | 7/2012 | Davenport et al. | |
| 9,199,053 | B1 * | 12/2015 | Allum | A61B 5/087 |
| 2002/0165482 | A1 * | 11/2002 | Keldmann | A61M 15/08 604/57 |
| 2003/0168067 | A1 | 9/2003 | Dougill et al. | |
| 2005/0066976 | A1 | 1/2005 | Wondka | |
| 2008/0051674 | A1 | 2/2008 | Davenport et al. | |
| 2008/0060649 | A1 | 3/2008 | Veliss et al. | |
| 2008/0223375 | A1 * | 9/2008 | Cortez | A61M 16/0672 128/207.18 |
| 2008/0257343 | A1 | 10/2008 | Peterson | |
| 2008/0276941 | A1 | 11/2008 | Doty et al. | |
| 2009/0183739 | A1 | 7/2009 | Wondka | |
| 2010/0242959 | A1 * | 9/2010 | Djupesland | A61M 15/0028 128/203.15 |
| 2011/0125052 | A1 | 5/2011 | Davenport et al. | |
| 2011/0126830 | A1 * | 6/2011 | Djupesland | A61M 15/0028 128/203.15 |
| 2011/0203591 | A1 * | 8/2011 | Amarasinghe | A61M 16/06 128/205.25 |
| 2012/0318270 | A1 | 12/2012 | McAuley et al. | |
| 2013/0190643 | A1 | 7/2013 | Brambilla | |
| 2013/0199531 | A1 | 8/2013 | Ramanathan et al. | |
| 2014/0000626 | A1 | 1/2014 | O'Connor et al. | |
| 2014/0116447 | A1 | 5/2014 | Cortez, Jr. et al. | |
| 2014/0158127 | A1 * | 6/2014 | Boucher | A61M 16/0683 128/203.22 |
| 2014/0360499 | A1 * | 12/2014 | Peets | A61M 16/0672 128/204.12 |
| 2015/0090255 | A1 * | 4/2015 | Gulliver | A61M 25/02 128/202.15 |

OTHER PUBLICATIONS

Mountainside Medical Equipment, Nasal Cannula with Flared Nasal Prongs with 7 foot Tubing, located at http://www.mountainside-medical.com/products/nasal-cannula-with-flared-nasal-tips-and . . . , printed Jan. 12, 2016, 2 pages.

Patterson Dental Supply, Inc., Monoject 450 Saliva Injectors, 250/Pkg—Covidien, www.pattersondental.com, date unavailable.

Putnam Plastics, Longitudinal Wire Reinforced Tube, https://www.flickr.com/photos/107297805@N06/11073923643, date unavailable.

Putnam Plastics, www.putnamplastics.com/galleries/images, date unavailable.

Salter Labs, Tender Grip—A unique skin fixation system designed to hold the cannula head tubing and facepiece in position. Salter Labs Website Advertisement. Copyright 2009 Salter Labs.

Tri-Med, Inc. Oxygen Nasal Cannulas, located at http://www.tri-medinc.com/nasal-cannula.htm?gclid=CJOY4sD57ckCFRAbgQodV10BUQ, printed Jan. 12, 2016, 4 pages.

PCT International Search Report and Written Opinion for PCT/US17/44631 dated Aug. 24, 2017 (14 pages).

* cited by examiner

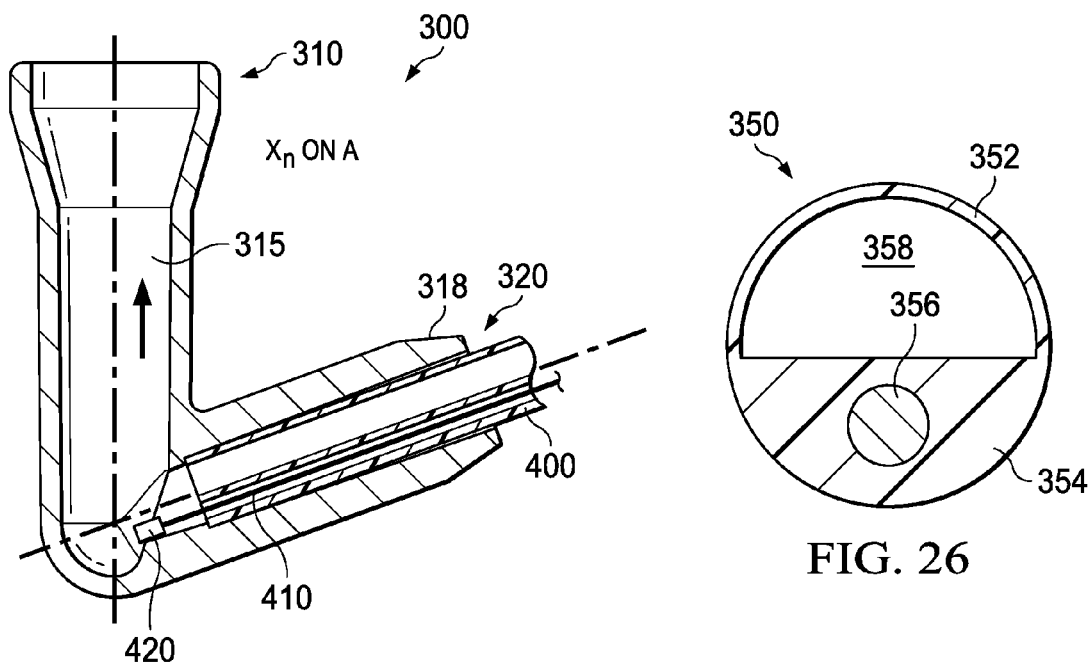
FIG. 25F
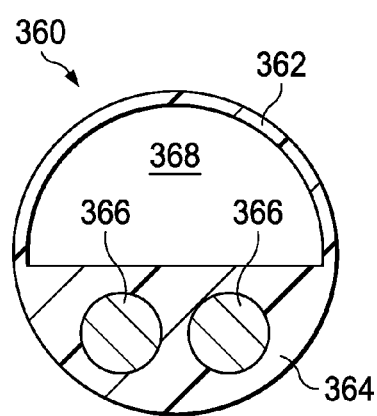
FIG. 26
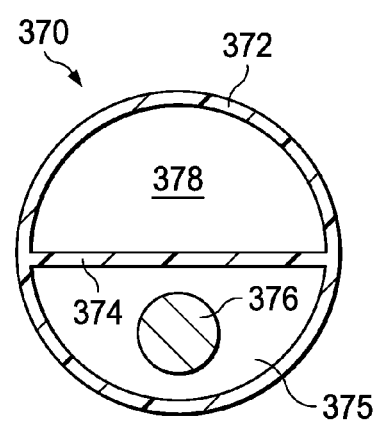
FIG. 27
FIG. 28

GAS DELIVERY DEVICE

CROSS-REFERENCE TO RELATED APPLICATIONS

This application is a continuation-in-part from U.S. application Ser. No. 14/599,228 filed Jan. 16, 2015, which is a continuation-in-part from U.S. application Ser. No. 13/944,226 filed Jul. 17, 2013, the disclosures of which are hereby incorporated by reference.

FIELD OF THE INVENTION

This application relates to an apparatus for supplying supplemental oxygen or other gas to a patient via a nasal cannula.

BACKGROUND OF THE INVENTION

A dual prong nasal cannula is generally used to deliver oxygen to a patient via the patient's nose. The most commonly used arrangement includes a dual prong nosepiece that is centered in a loop of vinyl tubing. The nosepiece prongs are inserted into the patient's nostrils with the tubing tucked behind the ears and then extending around to the front of the patient below the chin. A slide adjustment may be used to draw the tubing tight beneath the chin. Usually by the third or fourth day of using a dual prong nasal cannula, the skin and subcutaneous areas in contact with the cannula prongs and tubing become irritated. By the fifth day, the majority of patients begin to use tissues and the like to relieve the soreness, pressure and irritation under the nose and around the ears. This soreness, pressure and irritation is often due to abrasion and interface pressure, which is caused by continuous movement of the tight fitting tubing and cannula prongs and the accumulation of moisture between the skin and the tubing and/or cannula prongs. As the slide adjustment is pulled tighter to keep the cannula prongs positioned in the nostrils of the patient, the irritation is only exacerbated and the subcutaneous layers of the skin are affected.

Thus, the use of a conventional dual prong cannula can become quite uncomfortable for a patient and can lead to pressure ulcers at contact points. The comfort of the patient becomes even more critical, both to the patient and to the professionals attending the patient, when the patient is also fitted with a naso-gastric or Levine tube. In this event, the nose becomes a fairly cluttered access route, and adhesive tape is often used, by application to the face, to position all the tubes and secure them in place.

In addition to the discomfort and susceptibility to skin deterioration where supplemental oxygen is required, a patient may also suffer from "free floating anxiety" as a result of reduced blood oxygen. Such a patient may believe something is wrong but cannot quite identify the problem, and may not be thinking clearly. Often such patients have feelings of claustrophobia and may attempt to remove the nasal cannula despite the resulting adverse impact on the patient's condition. It is not uncommon to find the tubing disconnected or the cannula prongs displaced from the nose due to pulling on the cannula that results from the movement of the patient's head, especially during sleep. Further, patient non-compliance or lack of cooperation, resulting from irritation and discomfort caused by a nasal cannula, may necessitate the use of some more expensive or aggressive means of oxygen administration, including face masks or catheters.

To an increasing extent, supplemental oxygen is used on an outpatient basis, such as in a patient's home. Under such conditions, the cosmetic appearance of the oxygen delivery apparatus can be important, and the commonly-used dual prong cannula can make a person feel conspicuous and, as previously mentioned, cause irritation from interface pressure.

In addition to the discomfort, skin deterioration, and cosmetic concerns posed by use of dual prong cannulas, it has been established that using a single prong nasal cannula, or a unilateral, nasal catheter will provide a higher inspired oxygen fraction than a dual prong nasal cannula.

Furthermore, certain prior art gas delivery system designs have resulted in irritation and/or discomfort to the patient. For example, in the mid-1980's the medical industry relied on EKG patches to stabilize oxygen tubes and secure the end of a single prong cannula within the patient's nostril. While the EKG patches used a glue or adhesive that worked fine for EKGs, the EKG patches did not function well for use as a stabilization patch for securing oxygen tubing to the facial skin of a patient. When the EKG patches were used with gas delivery systems for extended periods of time, there was a risk that the adhesive could pull the patient's skin off upon removal of the stabilization patch, especially the skin of infants or elderly people.

When using prior art gas delivery systems, health care providers encountered difficulty with securing the plastic tubing component of the gas delivery systems to the patient's face. After the plastic tubing adapted to the patient' skin temperature, the plastic tubing become softer and lose integrity. This problem was amplified when the gas delivery system was used with patients having a fever, particularly with high temperatures, for example, of 101 degrees to 103 degrees. Once the plastic tubing lost its integrity, the cannula prongs would no longer be supported by the tubing and would fall out of the patient's nostril. A need exists for a gas delivery system that includes a mechanism for maintaining the tubing shape and integrity as the temperature of the tubing rises due to the patient's skin temperature.

Therefore, a need exists for a gas delivery device having a single prong nasal cannula, or a single prong gas delivery device, that can be securely and comfortably affixed to a patient while providing an adequate supply of oxygen or other gas to the patient with the least amount of irritation and/or discomfort to the patient possible and overcoming the problems associated with prior art oxygen nasal cannulas.

The relevant prior art includes the following references:

| Pat. No. | Inventor | Issue/Publication Date |
|---|---|---|
| (U.S. Pat. References) | | |
| 4,660,555 | Payton | Apr. 28, 1987 |
| 4,685,456 | Smart | Aug. 11, 1987 |
| 4,736,741 | Payton et al. | Apr. 12, 1988 |
| 4,742,824 | Payton et al. | May 10, 1988 |
| 6,804,866 | Lemke et al. | Oct. 19, 2004 |
| 6,807,966 | Wright | Oct. 26, 2004 |
| WO2005/014080 | Wood | Feb. 17, 2005 |
| 6,913,017 | Roberts | Jul. 5, 2005 |
| 2008/0223375 | Cortez et al. | Sep. 18, 2008 |
| D643,113 | Butler | Aug. 9, 2011 |

SUMMARY OF THE INVENTION

An exemplary embodiment of the present invention provides a gas delivery device comprising a single prong nasal cannula that can be securely affixed to a patient while providing an adequate supply of oxygen or other gas to the patient with the least possible amount of skin irritation and/or discomfort to the patient.

An exemplary embodiment of the present invention provides a gas delivery device comprising a single prong nasal cannula for insertion into a patient's right or left nostril to deliver oxygen or other gas to the patient. In one exemplary embodiment, a the gas delivery device includes a single tubular cannula prong or single tubular nasal cavity component that has a gas passageway, with a tubular wall surrounding the gas passageway, a first end of the single tubular nasal cavity component is adapted to be inserted a single nostril of a patient. A longitudinal body portion of the single tubular nasal cavity component extends between the first end and a second end, which second end is positioned outside the patient's nostril. A tubular guidance-stabilization system includes a longitudinal tubular conduit having a longitudinal gas passageway, with a tubular wall surrounding the gas passageway, and includes a first end that is connected to and in fluid communication with the second end of the nasal cavity component, and further includes a second end that is connected to and in fluid communication with an attachable gas supply or gas extension tube. A first stabilization patch secures the tubular guidance-stabilization system to the patient's face proximate the patient's cheek; and a second stabilization patch secures the tubular guidance-stabilization system behind the patient's ear at the tip of the mastoid. A bendable or flexible, thin wire is located within the tubular wall of the tubular guidance-stabilization system, and the thin flexible wire extends substantially axially along and within the tubular wall, beginning at the first end of the tubular guidance-stabilization system and terminating at a position approximately one inch below where the tubular guidance-stabilization system is secured behind the patient's ear.

In an alternative embodiment, the tubular guidance-stabilization system may have a flexible strap, made of metal, composite or other suitable material, located within the tubular wall of the longitudinal tubular conduit that extends substantially axially along and within the tubular wall. The purpose of the flexible wire or flexible strap is to support the plastic tubular conduit of the tubular guidance-stabilization system that has become flaccid as a result of being heated up by the patient's body temperature. In turn, the tubular guidance-stabilization system supports the integrity of the gas delivery device in order to maintain the tubular nasal cavity component in the patient's nostril. An exemplary embodiment of the tubular guidance-stabilization system is designed to allow the gas delivery device to be adjusted to skirt the patient's face and to be contoured to the patient's face and head, minimizing contact of device to the patient's skin.

During use by a patient, an exemplary embodiment of the tubular guidance-stabilization system provides guidance, stabilization, strain-relief and retention of the gas delivery device and supports the nasal cavity component within a single nostril of the patient. The flexible wire or flexible strap that is embedded (or otherwise inserted) within the wall of the longitudinal tubular conduit of the tubular guidance-stabilization system is isolated from the patient's skin, nose secretions, moisture and oxygen to avoid harm to the patient or damage or corrosion to the wire or strap. The single tubular nasal cavity component and the tubular guidance-stabilization system may be made of medical grade plastic materials, silicon or polyvinylchloride (PVC), a vinyl polymer, a silicone polymer, Urethanes, or other medical grade elastomeric plastic(s) that are Latex or DEHP free.

In another exemplary embodiment, the tubular nasal cavity component may be flexible and may be constructed of soft, pliable, bendable or shape memory materials to allow the nasal cavity component to retain its shape when manually configured during either the initial placement or the subsequent adjustment of the gas delivery device on the patient, to thereby allow the tubular nasal cavity component to be retained within the patient's nostril during clinical use.

In another exemplary embodiment, the tubular nasal cavity component may be formed to fit within one of the patient's nostril passageway and, based on the size of the patient's nostril, will be of a size and shape to provide soft and rounded surfaces to prevent membrane irritation when the nasal cavity component is inserted within the nasal cavity. For instance, the tubular nasal cavity component may have a first end that is inserted into the patient's nostril, where the first end has a funnel or trumpet shape or contour to securely fit in within the patient's nostril and promote the flow of gas into the patient. In an exemplary embodiment, the width and diameter (or cross-sectional area) of the opening of the first end of the nasal cavity component, which is inserted into the patient's nostril, may be larger than the width and diameter (or cross-sectional area) of the center portion of the longitudinal body and also larger than the width and diameter (or cross-sectional area) of the second end of the nasal cavity component. The funnel shape (frustoconical shape) or trumpet shape (flared shape) of the opening of the first end of the tubular nasal cavity component creates a diverging flow path to promote a diverging gas flow through such first end such that the oxygen or other gas, to be dispersed into the nasal cavity, flows in all directions instead of in a single, narrow flow path. A diverging flow path of gas into the nostril results in less irritation and less dryness and cracking of the inside of the nostril. Furthermore, the funnel shape or trumpet shape of the opening of the tubular nasal cavity component prevents or at least inhibits or reduces the risk of backflow or escape of the gas outside the nostril and into the ambient air, which in turn establishes a potentially greater nasal cavity reservoir of gas that is available for the patient's next breath.

In another exemplary embodiment, the gas delivery device includes a single U-shaped nasal cavity component that has a first end that is adapted to fit inside a patient's nostril, a second end, a first tubular section having a longitudinal axis, a bend portion, and a second tubular section having a longitudinal axis, wherein the first tubular section extends away from the first end toward the bend portion, the second tubular section extends from the bend portion to the second end. An angle between the longitudinal axis of the first tubular section and the longitudinal axis of the second tubular section is approximately seventy degrees (70°)±ten degrees (10°). Alternatively, the angle between the longitudinal axis of the first tubular section and the longitudinal axis of the second tubular section within nasal cavity component may range from about zero degrees (0°) and about one hundred eighty degrees (180°).

In another embodiment, the gas delivery device includes a substantially U-shaped portion that is adapted to extend downward from the patient's nostril, around an outer surface of the patient's nostril, and then extend upward toward the patient's eye. A tubular guidance-stabilization system is adapted to extend from the substantially U-shaped portion, across the patient's cheek and over the patient's ear. The substantially U-shaped portion may be integrally formed or molded within and made part of to be in fluid communication with the tubular nasal cavity component as described above. Alternatively, the substantially U-shaped portion may be integrally formed within and part of the tubular guidance-stabilization system. The term "U-shaped," as used herein, describes the relative shape of a nasal cavity component, a tubular guidance-stabilization system, or any portion of the nasal cavity component or a tubular guidance-stabilization system that is bent, formed or molded to resemble the shape of either a "U" or a "J" or a "V."

In a further exemplary embodiment, the gas delivery device includes a tubular nasal cavity component having a gas passageway, a tubular wall surrounding the gas passageway, a first end that is adapted to be inserted in either nostril of a patient, a longitudinal body portion between the first end and a second end. The second end is positioned outside the patient's nostril, and a flexible or bendable wire may be embedded within at least a portion of the tubular wall, with the wire extending substantially axially along at least a portion of the tubular wall.

The tubular nasal cavity component may be bent into shape and may retain the bent shape. Alternatively, the tubular nasal cavity component may return to its original shape after bending.

The tubular nasal cavity component may have a substantially seventy plus or minus ten degrees (70±10°) bend, wherein the tubular nasal cavity component is adapted to extend downward from the patient's nostril, around an outer surface of the patient's nostril, and then in an upward direction toward the patient's eye.

Alternatively, the gas delivery device may have a relatively straight tubular nasal cavity component that is connected to and in fluid communication with a tubular guidance-stabilization system that is adapted extend downward from the tubular nasal cavity component when in use by a patient, bend in an upward direction toward the patient's eye, and extend across the patient's cheek and over the patient's ear. A U-shaped bend portion having a substantially seventy degrees plus or minus ten degrees (70±10°) bend is formed within the tubular guidance-stabilization system. This bend prevents the formation of kinks and folding in the tubular guidance-stabilization system of the gas delivery device that could reduce or restrict the flow of gas and also enhances the support and placement of tubular nasal cavity component and tubular guidance-stabilization system on the patient's face.

In yet a further exemplary embodiment, when fitted to a patient, a secondary coiled section of flexible tubing may then extend from the tubular guidance-stabilization system downward to the patient's shoulder. The coiled section of tubing allows the patient to move his or her head without affecting the placement of (e.g., dislodging) the tubular nasal cavity component in the nostril.

In another exemplary embodiment, when fitted to a patient, a flexible piece of tubing extends from the tubular guidance-stabilization system, below the location where the tubular guidance-stabilization system is secured to the mastoid tip of the patient, on one side of the patient. The flexible tubing then extends around the back of the patient's neck and over to the opposite shoulder of the patient, where a clip located on the tubing may be used to attach the tubing to the patient's clothing, providing additional strain relief for the device. Finally, the flexible piece of tubing extends to the supply source for supplying oxygen or another gas. The clip may be positioned and moved along the tubing for optimal placement and attachment of the clip to the patient's clothing. The clip is used to prevent either the weight of the gas supply tubing or movement of the patient from moving or pulling on the gas delivery device and dislodging the nasal cavity component from the patient's nostril and causing irritation and/or discomfort to the patient.

In yet another embodiment of the present invention, a gas delivery device includes a substantially planar, semi-rigid stabilization patch having a clip or flap that further secures the tubular guidance-stabilization system to the cheek of the patient, when the gas delivery device is fitted to a patient. The clip or flap may be a semi-rigid substantially C-shaped clip located on an upper surface of the planar stabilization patch. The C-shaped clip is sized and configured to open to receive therein flexible tubing of the tubular guidance-stabilization system and to then close to hold the flexible tubing without pinching off gas delivery via the flexible tubing. The substantially planar stabilization patch has a patient safe adhesive located on a rear surface for attaching the patch to the patient's cheek. After the patch is secured to the patient's cheek, the tubular guidance-stabilization system may be pressed into the C-shaped clip and held in place. The substantially planar, semi-rigid stabilization patch may also have other sizes, shapes and means of holding the tubular guidance-stabilization system to the cheek, such as an adhesive, a hook and loop fastener, and so forth.

In another exemplary embodiment, the gas delivery device includes a flexible stabilization patch made of flexible, breathable and non-irritating material. The flexible stabilization patch may have a barbell shape with two patch sections that are separated and connected by a tubing securement area. The flexible stabilization patch may be placed on and secured to the patient's cheek and/or to the skin behind the patient's ear by an adhesive located on one side of a patch section. When fitted to a patient, the flexible stabilization patch having a barbell shape secures the tubular guidance-stabilization system to the face of the patient and over and behind the patient's ear by placing the tubular guidance-stabilization system along and perpendicularly across the tube securement area of the stabilization patch, folding the stabilization patch over the tubular guidance-stabilization system to mate the first patch section to the second patch section with an adhesive, and then affixing the stabilization patch on the skin using the adhesive located on the exposed side of a patch section. The flexible stabilization patch is preferably breathable, having tiny perforations for the health of the skin and for escape of fluids and heat. Alternatively, the patch may use water based adhesives.

The patch is approximately may be about one inch in diameter and may have release liner at the adhesive side that covers the medical grade adhesive to protect and promote the shelf-life of the patch. The adhesive side can be placed on the patient's skin and should hold the tubing for clinical periods of time (e.g., up to seven days) without significant irritation to the skin. The medical grade patches can be changed from time to time. The medical grade adhesive that is used does not damage the skin when the stabilization patch is removed from the patient's face. The medical grade adhesive is a self-stick adhesive that is suitable for the duration of its application and will adhere to the patient's skin. The composition of the medical grade adhesive may include polymers, medical grade solvents, and/or water based coating systems.

In another exemplary embodiment, the gas delivery device includes a one-piece flexible stabilization patch made of flexible, breathable and non-irritating material, with a patient-friendly adhesive located on one-side of the patch. The flexible stabilization patch is preferably breathable, having tiny perforations for the health of the skin and for escape of fluids and heat. The one-piece flexible stabilization patch may be about one inch in diameter and may have a peel off protective covering on the adhesive side, on which a medical adhesive or glue is applied. The flexible stabilization patch is used to secure the tubular guidance-stabilization system onto the tip of the patient's cheek bone and behind the lower portion of the patient's ear proximate the mastoid tip, where there is no hair and little oil. For instance, after removing the peel off protective covering from the adhesive side of the stabilization patch, a medical provider will first position the tubular guidance-stabilization system at the tip of the cheek bone as described herein and then cover the portion of the guidance-stabilization system on the tip of the cheek bone with the adhesive side of the patch and firmly press the remainder of the exposed patch onto the patient's skin.

In another exemplary embodiment, the gas delivery device is secured and stabilized at three locations, namely by securing the tubular guidance-stabilization system at the tip of the cheekbone with a stabilization patch, by securing the tubular guidance-stabilization system at the tip of the mastoid (located behind the lower part of the patient's ear where no hair is located) with a stabilization patch, and by clipping the tubular guidance-stabilization system to the patient's clothing on the shoulder that is opposite of where the tubular guidance-stabilization system is secured at the tip of the mastoid.

In another exemplary embodiment of the invention, the gas delivery system includes an adapter for connecting the gas delivery system to an oxygen or gas supply source. There is a global specification for male and female connectors that establishes specific dimensions of male and female adapters. The gas delivery system may include the male side of the adapter at its terminal end, which mates with a female adapter that is located on gas supply tubing or in a wall mounted adapter that runs to the gas source.

The design of the gas delivery system allows for interchangeability to either nostril to reduce skin irritation from the contact of the medical grade plastic materials to the human skin and within the nasal cavity.

The guidance-stabilization system may have internal or external keys to properly align, during assembly or adjustment of the gas delivery device, the guidance-stabilization system with the nasal cavity component, which has a corresponding external or internal groove or slot. The connection between the guidance-stabilization system and the nasal cavity component insures ease of use and correct placement of device through-out the clinical time period.

In one embodiment of the invention, in forming the connection between the guidance-stabilization system and the nasal cavity component, the end of the tubular guidance-stabilization system acts as the female portion of the connection and corresponding end of the nasal cavity component acts as the male portion of the connection. Alternatively, in forming the connection between the guidance-stabilization system and the nasal cavity component, the end of the tubular guidance-stabilization system acts as the male portion of the connection and the corresponding end of the nasal cavity component acts as the female portion of the connection.

In a further exemplary embodiment, there is provided a system for delivery of a gas to a patient that has a single tubular nasal cavity component having only two terminal ends, including one end for gas inlet and one end for gas outlet. A single gas flow path extends from the gas inlet to the gas outlet ends. The tubular nasal component is configured for insertion into a nostril of a patient and adapted to maintain an inserted position without adhesive. The single tubular nasal cavity component includes:

a first portion having a first longitudinal axis along the single gas flow path, a proximal end of the first portion flared outward and configured for insertion into a nostril of a patient, and a second portion having a second longitudinal axis, the second portion having a gas inlet end to receive gas from a gas supply, a distal end of the second portion intersecting a distal end of the first portion in a bend portion, such that the second longitudinal axis and the first longitudinal axis intersect at an angle of between about 60 and about 80°.

Optionally, the cannula of the system has a substantially frusto-conical outward flaring tip crowned with a substantially cylindrical tip. Optionally, the cylindrical tip includes a rounded curvature at an upper extremity thereof. Further optionally, an inner surface of the distal end of the first portion is smoothly curved, as seen in side cross section, up to an intersection with an inner surface of the distal end of the second portion. The smoothly rounded curvature may terminate at a tangent to the inner surface of the distal end of the second portion at an angle of about 16 to about 20 degrees to the first longitudinal axis.

Optionally, the length of the first portion is about 3 to about 2 times an internal diameter D of the proximal end. Optionally, the length of the second portion is about 1.7 to about 1.2 times an internal diameter D of the proximal end.

In addition, and optionally, the system may include gas supply tubing attached to the gas inlet end of the second portion The gas supply tubing may at least one flexible wire inserted along a length thereof, the gas supply tubing having a length to extend from the gas inlet end of the second portion end of the nasal cavity component, across the cheek of the user, and over the ear of the user such that during use, the at least one flexible wire maintains a configuration of the gas supply tubing for supporting secure placement of the nasal cavity component in a nostril of a user, and gas flows from the gas supply tubing to the single gas flow path in the nasal cavity component.

Additionally, the system may include at least one sensor in proximity to or in the nasal cavity component, and the at least one flexible electricity-conducting conduit is in communication with the at least one sensor. The at least one flexible electricity conducting conduit may be comprised of metal or an electricity-conducting polymer. The exemplary system further may include at least one sensor in proximity to or in the nasal cavity component. The at least one sensor may transmit sensed data wirelessly.

Optionally, the exemplary system for delivery of a gas to a patient of has the tip and the length of the first portion each sized such that air flows around the nasal cannula when the nasal cannula is inserted in a nostril of a user. Optionally, the tip and the length of the first portion are each sized such that gas exits from the nasal cannula in a vortex flow pattern when the nasal cannula is in use. Optionally when the gas includes oxygen, the vortex flow of the oxygen-containing gas increases oxygen intake by the user, as compared to using a nasal cannula without a vortex flow.

Positive end expiratory pressure ("PEEP") is enhanced by the single nasal cannula, especially the tip. It is theorized, without being bound, that the design, size and shape of the cannula tip delivers oxygen within the upper nasal vestibule to enhance the anatomical PEEP, first within the nasal vestibule, and secondly, within the upper nasal cavity. The nasal cannula shape and material selection is designed to increase the anatomical positive airway pressure that in turn improves oxygen absorption in the lungs. The nasal cannula also provides a continuous positive airway pressure ("CPAP") through direct injection of balanced atmospheric oxygen, during inspiration and expiration cycles, within the nasal vestibule and upper nasal cavity. An increase in oxygen absorption may be detected by measuring blood oxygen saturation using Pulse Oximetry.

The gas delivery device can be used to supply oxygen and other gas, such as nitrous oxide or other anesthesia, to a patient. When using the gas delivery device to supply oxygen, it may be desirable to avoid fully blocking the nostril with the nasal cavity component, providing partial occlusion of the nostril. When using the gas delivery device to supply anesthesia, however, it may be desirable to completely block the nostril with the nasal cavity component, providing full occlusion of the nostril.

The above and other objects, features and advantages of the present invention should become even more readily apparent to those skilled in the art upon a reading of the following detailed description in conjunction with the drawings wherein there is shown and described illustrative embodiments of the invention.

BRIEF DESCRIPTION OF THE DRAWINGS

In the following detailed description, reference will be made to the attached drawings in which:

FIG. 25 B is an end view from the gas inlet side of the component of FIG. 25 A.

FIG. 25 C is a top view of the component of FIG. 25 A.

FIG. 25 D is a side cross-sectional side view taken along 25E-25E of FIG. 25B.

FIG. 25 E is an enlarged view of a portion shown in dashed lines in FIG. 25 D.

FIG. 25 F is a side cross sectional view of the component of FIG. 25 A depicting an example of a sensor and an example of a connected signal transmitting cable.

FIG. 26 is an exemplary embodiment of a cross section through a gas supply tubing showing a cable therein effective as an electricity and signal transmitting conduit.

FIG. 27 is an exemplary embodiment of a cross section through a gas supply tubing showing a pair of cables therein effective as an electricity and signal transmitting conduit.

FIG. 28 is an exemplary embodiment of a cross section through a gas supply tubing showing a cable therein effective as an electricity and signal transmitting conduit.

DETAILED DESCRIPTION OF EXEMPLARY EMBODIMENTS

Figure 1:
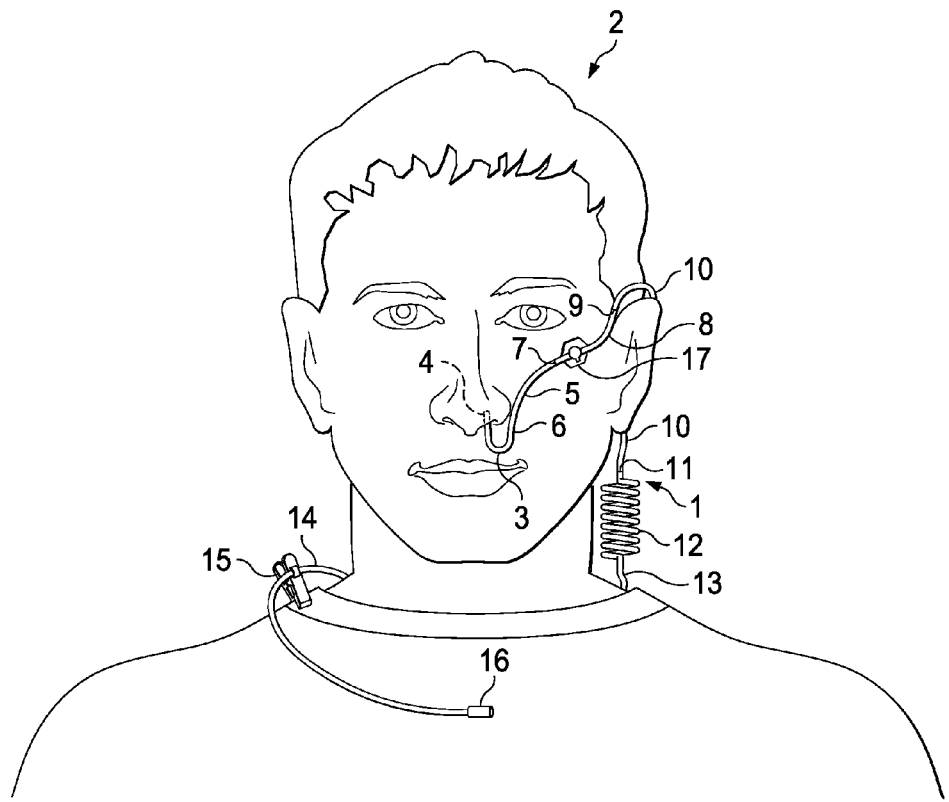
FIG. 1 is a front view of a gas delivery device of the present invention being worn by a patient.
Figure 2:
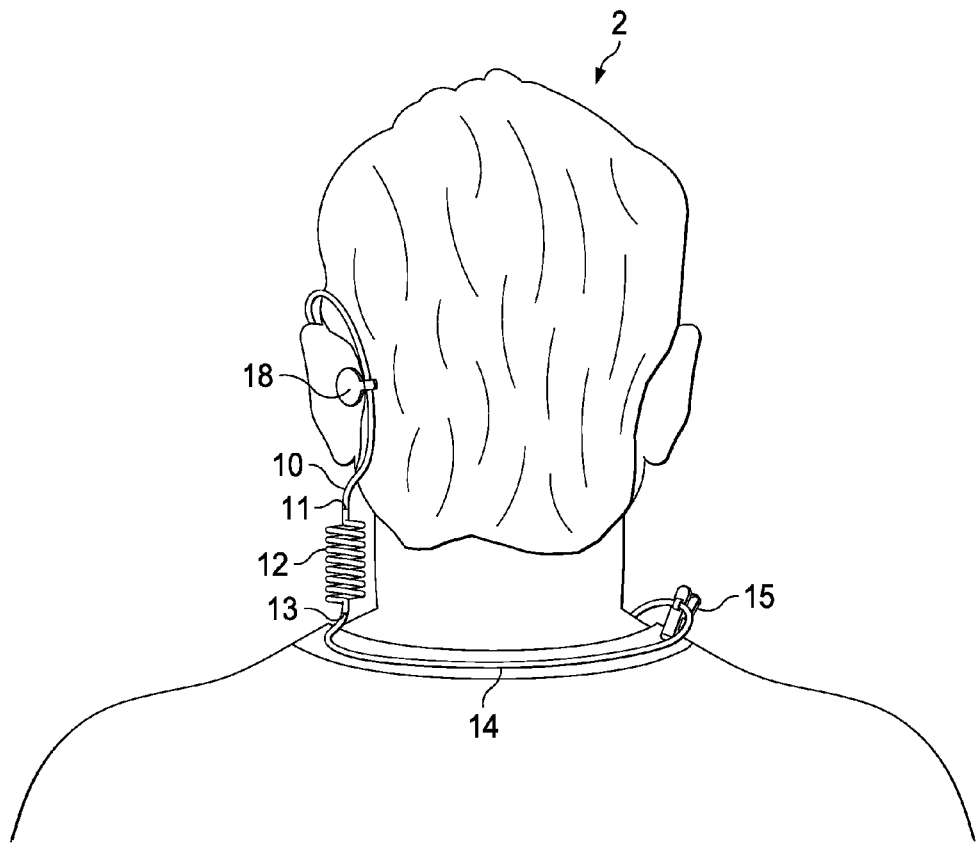
FIG. 2 is a rear view of a gas delivery device of the present invention being worn by a patient.

With reference to FIGS. 1 and 2, a front view and a rear view, respectively, of one embodiment of a single prong gas delivery device 1 of the present invention being worn by a patient 2 is illustrated. The gas delivery device 1 comprises a single substantially U-shaped nasal cavity component 3 that may be non-flexible or flexible and may be inserted into either nostril of the patient 2 to deliver oxygen or other gas to the patient. The substantially U-shaped nasal cavity component 3 is preferably constructed from formable or memory material.

In one embodiment, the nasal cavity component 3 is tubular. As further described herein, the substantially U-shaped nasal cavity component 3 may have a bendable or flexible wire 19 embedded within at least a portion of the tubular wall 20, with the wire 19 extending substantially axially along the tubular wall 20. With the use of a wire 19 in a nasal cavity component (and with the -tubular guidance-stabilization system, as described below), softer and more flexible materials, which in turn are more comfortable and less irritating to the patient, may be used. Such materials may include a vinyl polymer or a silicone polymer.

The substantially U-shaped nasal cavity component 3 has a first end 4 that fits inside the patient's nostril and a second end 6 that is exterior to the nostril and extends downward from the patient's nostril, around an outer surface of the patient's nostril, and upward toward the patient's eye. The substantially U-shaped nasal cavity component 3 attaches to flexible and preferably formable or bendable tubing 8, also referred to herein as the tubular guidance-stabilization system. The tubular guidance-stabilization system 8 then extends upward from the second end 6 of the nasal cavity component 3 and toward the patient's eye or ear. The substantially U-shaped nasal cavity component 3 has a first end 4 that fits inside the nostril from which oxygen or other gasses are delivered to the patient.

The second end 6 of the U-shaped nasal cavity component 3 may further comprise a substantially ninety degree bend 5 preferably constructed from the same material as the rest of the substantially U-shaped nasal cavity component 3 to prevent formation of kinks which could reduce or restrict the flow of oxygen or other gas and to enhance placement of the nasal cavity component within the patient's nostril and the tubular guidance-stabilization system on the patient's face. The substantially U-shaped nasal cavity component second end 6 is joined at the juncture 7 of nasal cavity component 3 to the first section of tubular guidance-stabilization system 8.

In a preferred embodiment, the first section of the tubular guidance-stabilization system 8, which is preferably flexible, formable or bendable tubing, and which may have a bendable wire 32 (not shown) embedded in the wall 33 of the longitudinal tubular conduit of the tubular guidance-stabilization system, extends from a second end 6 of the U-shaped nasal cavity component across the patient's cheek (where the tubular guidance-stabilization system is secured by a stabilization patch, as described below), around the side of the face and toward the top of the patient's ear. The first section of tubular guidance-stabilization system 8 may be contoured over the patient's ear and bent slightly inward against the patient's scalp behind the ear to the mastoid tip (where the tubular guidance-stabilization system is further secured by a stabilization patch, as described below). This configuration allows the tubular guidance-stabilization system 8 to be positioned and worn slightly above the ear, thereby preventing interface pressure and friction behind the ear and allowing a patient to wear eye glasses without interference from the tubular guidance-stabilization system.

Alternatively, the first section of the tubular guidance-stabilization system 8 may be joined at juncture 9 to a second section of the tubular guidance-stabilization system 10. The second section of the tubular guidance-stabilization system 10 extends over and behind the ear and may be flexible, formable or bendable so that it may be contoured over the ear and bent slightly inward against the patient's scalp behind the ear to secure the tubing placement. This configuration of the second section of the tubular guidance-stabilization system 10 allows the tubing to be worn slightly above the ear, thereby preventing interface pressure and friction behind the ear and allowing a patient to wear eye glasses without interference from the tubing. A second section of the tubular guidance-stabilization system 10 is affixed to a third section of the tubular guidance-stabilization system 12 at a juncture 11. The third section of the tubular guidance-stabilization system 12 preferably consists of coiled flexible tubing which allows the patient to move his or her head without affecting the placement of the U-shaped nasal cavity component 3 in the nostril. A third section of the tubular guidance-stabilization system 12 is joined at juncture 13 to a fourth section of the tubular guidance-stabilization system 14. A fourth section of the tubular guidance-stabilization system 14 extends directly to the gas supply source and is preferably draped across the back of the patient's neck and crossing to the shoulder of the patient that is opposite to the side of the patient's nostril into which the nasal cavity component 3 is inserted, and thence to the gas supply source. A clip 15 may be used to attach the fourth section of tubing 14 to the patient's clothing, further securing and stabilizing the tubular guidance-stabilization system to patient and, in turn, securing the placement of the nasal cavity component 3 within the nostril. A fourth section of the tubular guidance-stabilization system 14 is attached to the gas supply at connector 16. Also illustrated in FIG. 1 is a semi-rigid stabilization patch 17 on the patient's face that further secures the tubular guidance-stabilization system 8 to the cheek of the patient and is discussed in greater detail below. Alternatively, a flexible stabilization patch 18 may be used to secure the tubular guidance-stabilization system 8 to the patient's cheek.

In an alternate embodiment, the first section of the tubular guidance-stabilization system 8 extends from a second end 6 of the U-shaped nasal cavity component across the patient's cheek (where the tubular guidance-stabilization system is secured by a stabilization patch, as described below), around the side of the face and toward the top of the patient's ear. The first section of tubular guidance-stabilization system 8 may be contoured over the patient's ear and bent slightly inward against the patient's scalp behind the ear to the mastoid tip (where the tubular guidance-stabilization system is further secured by a stabilization patch, as described below), and joined to a gas supply tubing.

In another preferred embodiment, a substantially U-shaped nasal cavity component 3 is tubular and includes a bendable wire 19 that is embedded within at least a portion of the nasal cavity component wall 20 and extends substantially axially along the nasal cavity component wall 20, a first end 4 that fits inside the patient's nostril and a second end 6 that is exterior to the nostril. The second end 6 of the nasal cavity component 3 extends downward from the patient's nostril, around an outer surface of the patient's nostril, upward toward the patient's eye to a substantially 90 degree bend 5 across the patient's cheek, around the side of the face, toward the top of and over the patient's ear. With this alternative embodiment, there is no juncture with a separate tubular guidance-stabilization system 8 proximate the patient's cheek, which eliminates a potential source of irritation for the patient.

With reference to FIG. 2, a rear view of an gas delivery device of the present invention being worn by a patient, a flexible stabilization patch 18 affixed behind the patient's ear is illustrated. This flexible stabilization patch 18 functions to additionally secure the tubing placed over the ear and reduce the movement of the tubing in the vicinity of the ear, reducing the interface pressure and friction of the tubing against the skin.

Figures 3, 4:
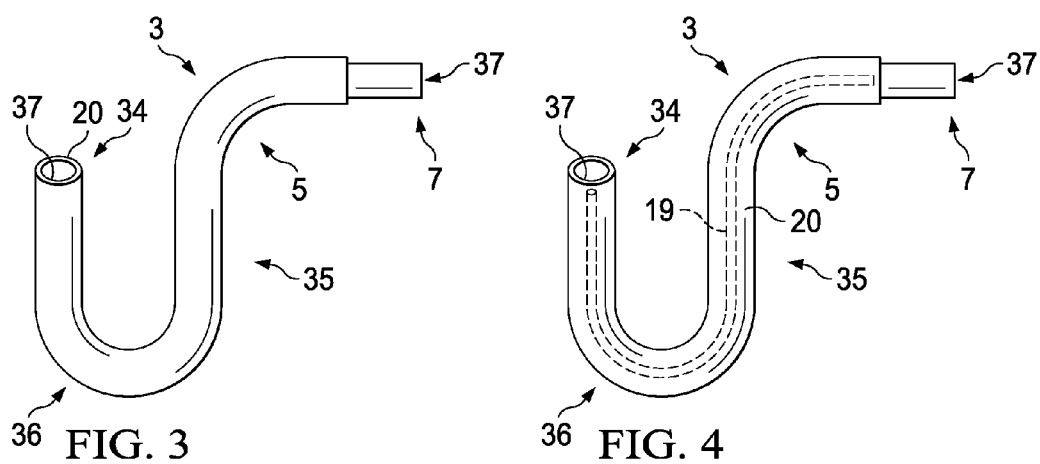
FIG. 3 is a side view of a U-shaped tubular nasal cavity component of the present invention constructed of a non-flexible material.
FIG. 4 is a side view of a U-shaped tubular nasal cavity component of the present invention constructed of a flexible, formable, or memory material.

With reference to FIG. 3, a side view of a U-shaped nasal cavity component 3 of the present invention constructed out of non-flexible tubing is illustrated, which is self-explanatory when viewed in conjunction with the description above. In an exemplary embodiment, the nasal cavity component 3 is tubing that is flexible and constructed out of formable or shape-memory material.

The nasal cavity component 3 has a first end 34, which is adapted to fit inside the patient's nostril, and a second end 35 having a substantially U-shaped portion 36, which that is adapted to extend downward from the patient's nostril, around an outer surface of the patient's nostril, and then upward toward the patient's eye. A nasal cavity component wall 20 surrounds the gas passageway 37. Also shown in FIG. 3 is a substantially ninety degree bend 5 in the second end 35. Also shown is the location of the juncture 7 of the U-shaped nasal cavity component 3 to first section of tubing (not shown). The length of the nasal cavity component extends from the first end 34 to the location of the juncture 7.

With reference to FIG. 4, a side view of a substantially U-shaped nasal cavity component 3 of the present invention is illustrated. The nasal cavity component 3 is a flexible tubing that is constructed out of a formable or shape-memory material. The nasal cavity component 3 has a first end 34, which is adapted to fit inside the patient's nostril, and a second end 35 having a substantially U-shaped portion 36, which that is adapted to extend downward from the patient's nostril, around an outer surface of the patient's nostril, and then upward toward the patient's eye. A nasal cavity component wall 20 surrounds the gas passageway 37. Also shown in FIG. 4 is a substantially ninety degree bend 5 in the second end 35. Also shown is the location of the juncture 7 of the U-shaped nasal cavity component 3 to a tubular guidance-stabilization system (not shown). The length of the nasal cavity component extends from the first end 34 to the location of the juncture 7. As illustrated here, there is a flexible or bendable wire 19 embedded in a wall 20 or proximal to the wall 20 of the U-shaped nasal cavity component 3. The wire 19 extends substantially axially along the tubular wall 20 of the nasal cavity component 3. The length of the wire 19 is typically less than the length of the nasal cavity component 3 so that the wire does not protrude into the patient's nostril and potentially harm the patient.

In one embodiment, the substantially U-shaped nasal cavity component 3 retains its shape when bent and in another embodiment the substantially U-shaped nasal cavity component 3 returns to its original shape after bending. The material used to form the flexible, formable or memory tubing of the nasal cavity component 3 may also be a semi-rigid plastic, polyurethane, elastomer or other material that retains its shape when bent without the assistance of the embedded flexible wire 19. Such tubing may also be applied to the section of tubing 10 that fits over the ear of the patient.

Figure 5:
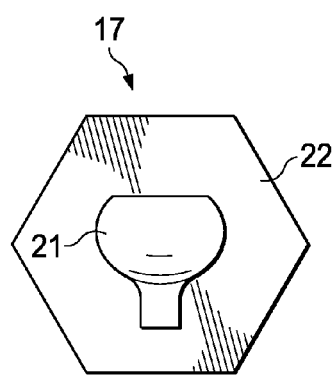
FIG. 5 is a front view of a semi-rigid stabilization patch of the present invention.
Figure 6:
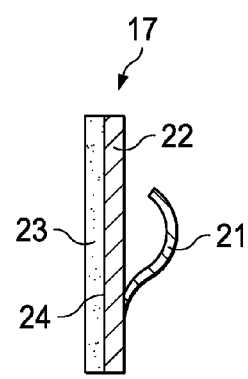
FIG. 6 is a side view of a semi-rigid stabilization patch of the present invention.

With reference to FIGS. 5 and 6, a front view and a side view, respectively, of a substantially planar, semi-rigid stabilization patch 17 is illustrated. The substantially planar, semi-rigid stabilization patch 17 comprises a semi-rigid substantially C-shaped clip 21 located on an upper surface 22 of a stabilization patch 17 and a patient-safe adhesive 23 located on a rear surface 24 to attach the stabilization patch 17 to a patient's cheek, as illustrated in FIG. 1. The first section of tubing 8 may be pressed into the C-shaped clip 21 and held in place by a pressure fit, as illustrated in FIG. 1. The C-shaped clip is sized and configured to open to receive therein flexible tubing of the tubular guidance-stabilization system and to then close to hold the flexible tubing without pinching off gas delivery via the flexible tubing. The planar stabilization patch may also have other means of holding the tubular guidance-stabilization system to the cheek, such as an adhesive, a hook and loop fastener, and so forth. One or more stabilization patches 17 or 18 (as described below) may be placed on a patient's cheek to stabilize the tubing. The placement of the tubing is over areas of the face that have minimum hair growth and oil secretion, thereby ensuring the one or more stabilization patches 17 or 18 adhere to the patient's skin.

Figure 7:
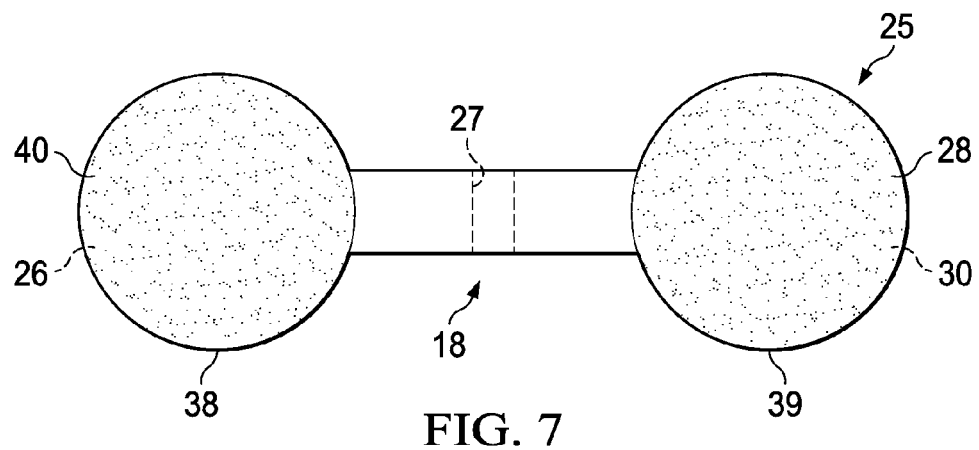
FIG. 7 is an open view of a flexible stabilization patch of the present invention.

With reference to FIG. 7, a flexible stabilization patch 18 in an open configuration 25 is illustrated. The flexible stabilization patch 18 may be affixed to the face as shown in FIG. 1 in replacement of the semi-rigid stabilization patch 17 and/or behind the patient's ear 18 as shown in FIG. 2. The flexible stabilization patch 18 preferably should be made of flexible, breathable and non-irritating material. The flexible stabilization patch 18 has two patch sections, a first patch section 38 and a second patch section 39, that are separated and connected by a tubing securement area 27. The flexible stabilization patch may have a barbell shape with two patch sections that are separated and connected by a tubing securement area 27. The first patch section 38 includes a skin adhesive side 26, which has adhesive on the surface for attaching the stabilization patch to the skin, and an opposing folding adhesive side 40. The second patch section 39 includes a folding adhesive side 28 and an opposing non-adhesive side 30.

Figure 8:
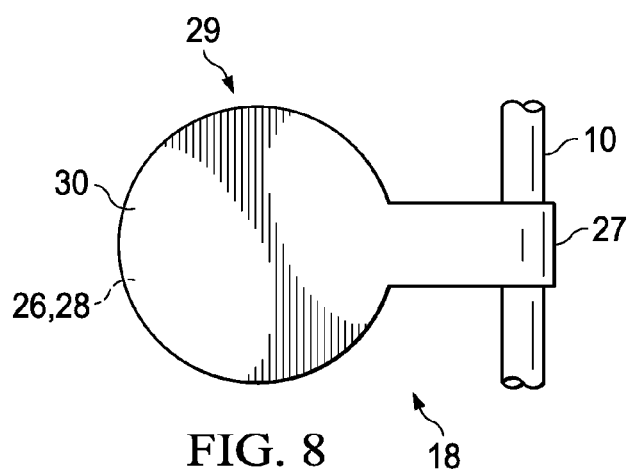
FIG. 8 is a closed view of a flexible stabilization patch of the present invention.

With reference to FIG. 8, a flexible stabilization patch 18 in a closed configuration 29 is illustrated. To achieve the closed configuration 29, the tubing 10 to be secured is placed perpendicularly across the tubing securement area 27. Then the flexible stabilization patch is folded over the tubing 10 so that the folding adhesive side 40 of the first patch section 38 is mated to the folding adhesive side 28 of the second patch section using an adhesive. The adhesive, which is used to mate the folding adhesive side 40 of the first patch section 38 to the folding adhesive side 28 of the second patch section 39, is located on the surface of either the first patch section 38 folding adhesive side 40 or the second patch section 39 folding adhesive side 28, or both. In a closed configuration, the flexible stabilization patch 25 secures the tubing 10 in the tubing securement area 27. Furthermore, the flexible stabilization patch is affixed to the patient's cheek or to the skin behind the patient's ear by placing the skin adhesive side 26 of the first patch section 18 onto the cheek or the skin behind the ear, respectively.

Figure 12:
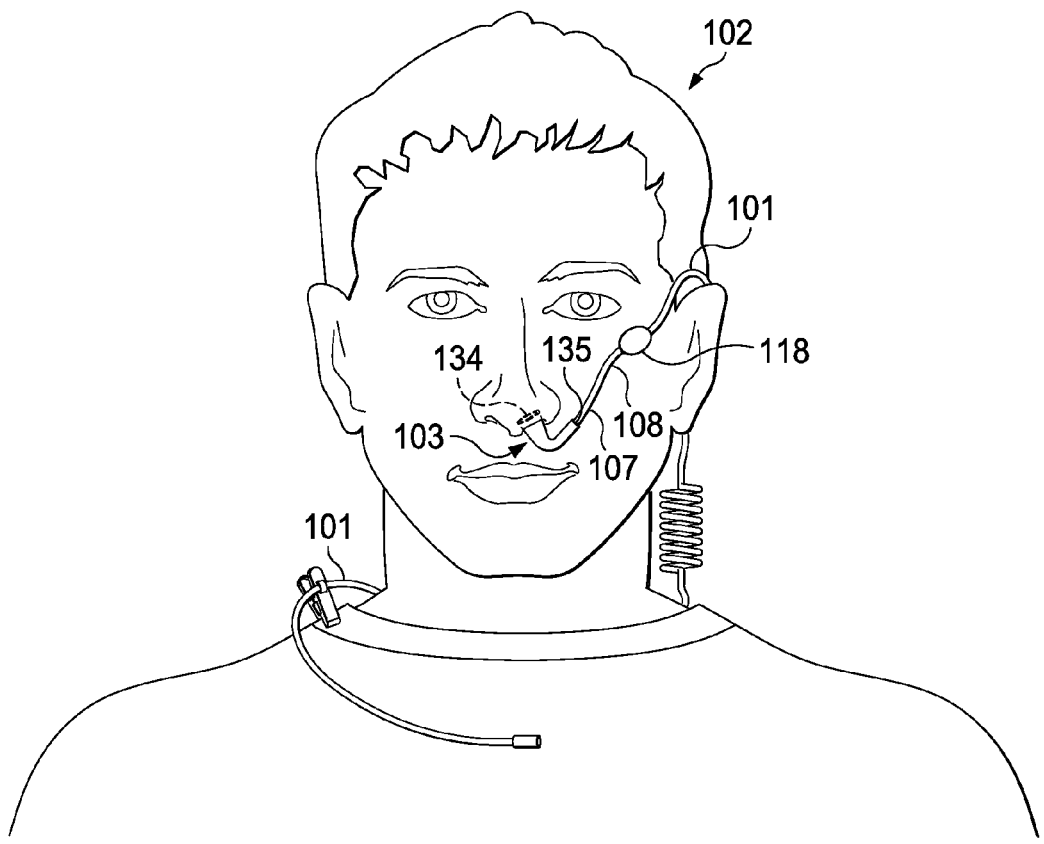
FIG. 12 is a front view of a gas delivery device of the present invention being worn by a patient.

In one embodiment, when the flexible stabilization patch 18 is a closed configuration as illustrated in FIG. 8, the secured tubing 10 is free to move relative to the flexible stabilization patch and shift in an axial direction relative to the tubing. In another embodiment, all movement of the secured tubing 10 relative to the flexible stabilization patch 118 (as depicted in FIG. 12, described herein) is prevented. In the closed configuration 25 of the flexible stabilization patch 18 in FIG. 8, the opposing non-adhesive upper surface 30 of the flexible stabilization patch 29 is exposed. The flexible stabilization patch is preferably breathable, having tiny perforations for the health of the skin and for escape of fluids and heat. The patch may be about one inch in diameter and may have a peel-off adhesive side, on which a medical adhesive is applied. The adhesive can be placed on the patient's skin and should hold the tubing for up to about seven days without significant irritation to the skin. The medical adhesive that is used does not damage the skin when the stabilization patch is removed from the patient's face.

Figure 9:
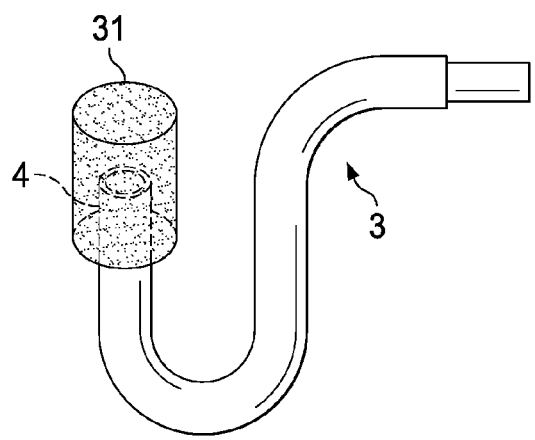
FIG. 9 is a side view of a U-shaped tubular nasal cavity component with a cannula tip of the present invention attached and constructed of pliable material.

With reference to FIG. 9, a side view of one embodiment of a U-shaped nasal cavity component 3 with a separate tip 31 affixed. The tip 31 is preferably made of pliable or formable materials which may be affixed to the end of the nasal cavity component 4. The tip 31 secures the nasal cavity component 4 within the nostril and enhances the inspired oxygen by reducing the backflow of oxygen out of the nostril.

Figure 10A:
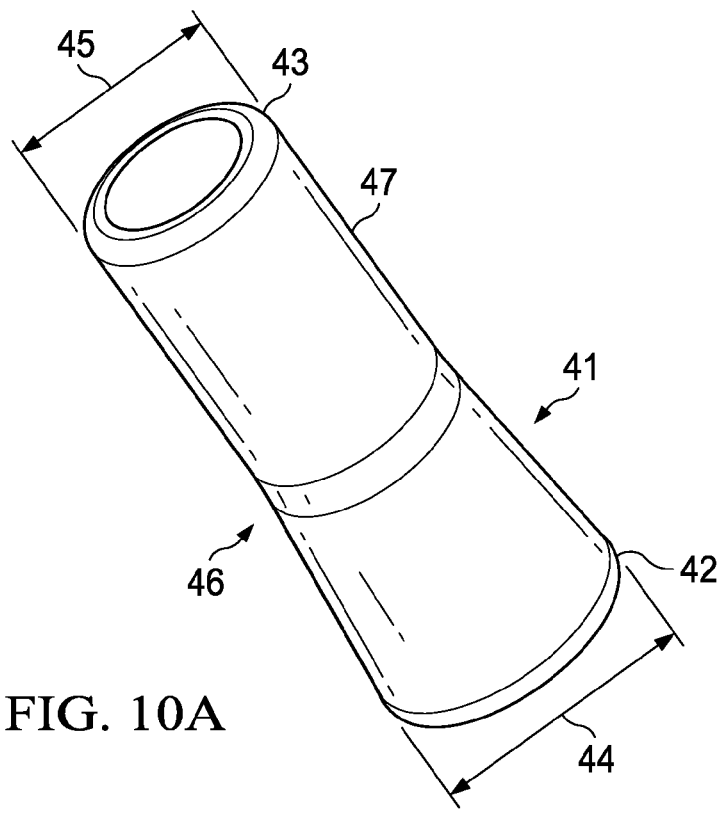
FIG. 10A is a perspective of a tubular nasal cavity component of the present invention.
Figure 10B:
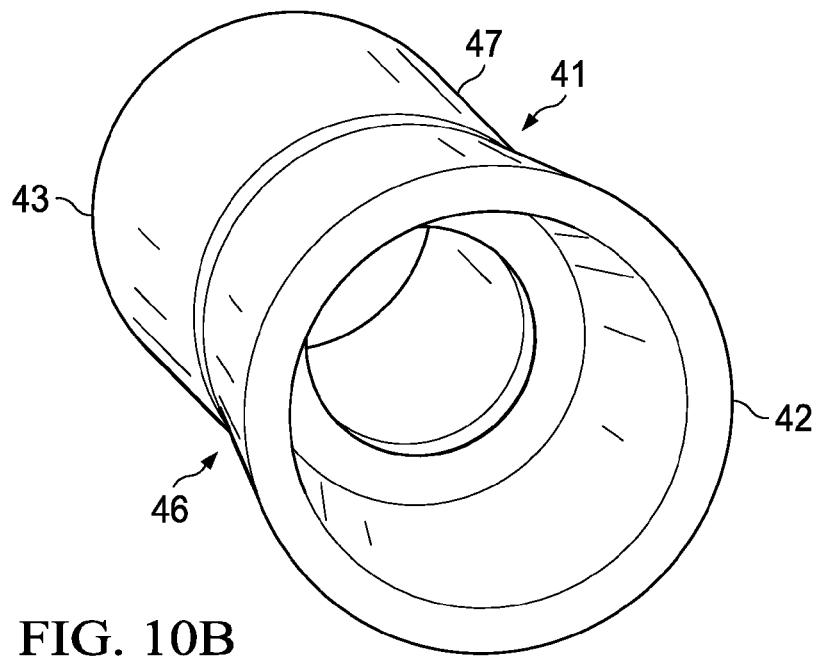
FIG. 10B is a perspective of a tubular nasal cavity component of the present invention.

With reference to FIG. 10A and FIG. 10B, each a perspective of another embodiment of a tubular nasal cavity component 41 is illustrated. The tubular nasal cavity component 41 may be of a size and shape to provide soft and rounded surfaces to prevent membrane irritation when the nasal cavity component is inserted within the nasal cavity. For instance, the tubular nasal cavity component may have a first end 42 that is inserted into the patient's nostril, where the first end 42 has a funnel shape or contour (a frustoconical shape) to securely fit in the patient's nostril, create a diverging flow path for the gas, and promote the flow of gas to the patient. The tubular nasal cavity component 41 has a longitudinal body 47, a first end 42 and a second end 43. The first end 42 of the nasal cavity component 41 has a width 44 and is adapted to be placed in a patient's nostril. The second end 43 of the tubular nasal cavity component 41 has a width 45 and is attached to and is in fluid communication with the tubular guidance-stabilization system (not shown). The first end 41 typically has a width 44, which is larger than the width 45 of the second end 43 of the nasal cavity component tip 41. In an exemplary embodiment, the width and diameter (or cross-sectional area) of the opening of the first end 42 of the nasal cavity component 41, which is inserted into the patient's nostril, may be larger than the width and diameter (or cross-sectional area) of the central portion 46 of the longitudinal body 47 and also larger than the width and diameter (or cross-sectional area) of the second end 45 of the nasal cavity component 41.

The funnel shape (frustoconical shape) of the opening of the first end 42 of the tubular nasal cavity component 41 creates a diverging flow path for the gas and allows a diverging gas flow through the first end 42 such that the oxygen or other gas to be dispersed into the nasal cavity flows in all directions instead of in a single, narrow flow path. A diverging flow of gas into the nostril results in less irritation and less dryness and cracking of the inside of the nostril. Furthermore, the funnel shape of the opening at the first end 42 of the tubular nasal cavity component 41 prevents or at least reduces the risk of backflow or escape of the gas outside the nostril and into the ambient air, which in turn establishes a potentially greater nasal cavity reservoir of gas that is available for the patient's next breath. Accordingly, the specific size and shape of the nasal cavity component 41 to be used for a specific patient may be selected according to the size of the patient's nostril (not shown) to comfortably secure the nasal cavity component in the nostril while mitigating any irritation and/or discomfort to the patient. For some patients, a nasal cavity component tip 41 will be selected so that the width 44 of the first end 42 of the nasal cavity component tip 41 is greater than the width 45 of the second end 43.

Figure 11:
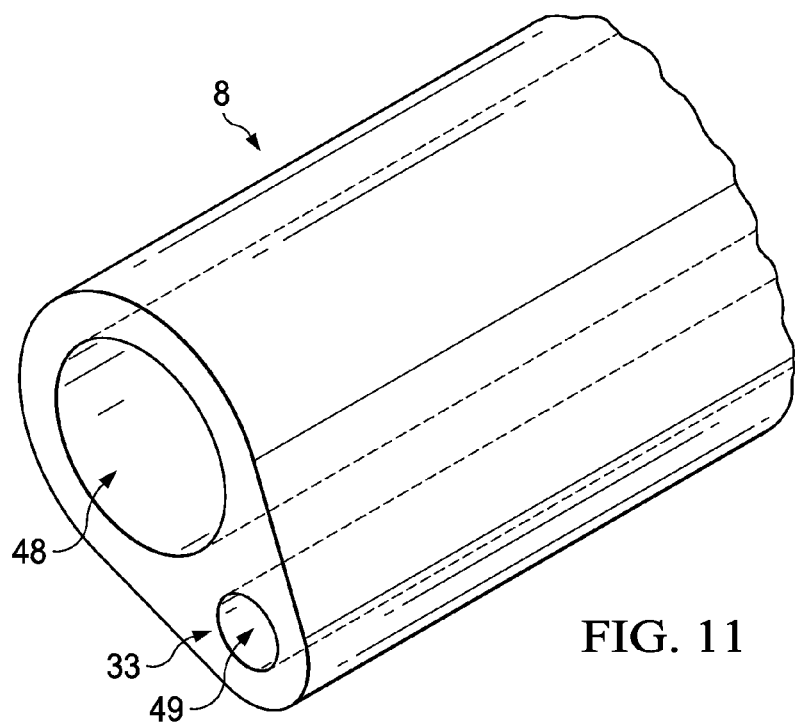
FIG. 11 is a perspective of a first section of a tubular guidance-stabilization system of the present invention, showing a tubing wall in which a bendable wire may be embedded.

With reference to FIG. 11, a perspective of a first section of the tubular guidance-stabilization system 8 of the present invention is illustrated, showing a gas passageway 48, a tubular wall 33 surrounding the gas passageway 48, and a separate duct or channel 49 in the tubing wall 33 into which a bendable, flexible wire (not shown) may be inserted and/or embedded. A plug (not shown) may be inserted into the end of the duct 49 and used to prevent protrusion of an inserted flexible wire 32 from the tubing 8. Alternatively, the flexible wire may be embedded into the tubular wall 33 of the tubular guidance-stabilization system 8 during the manufacturing process. Although the tubular wall 33 of the guidance-stabilization system 8 is illustrated as having a circular opening and cross-sectional area for flow, the tubular may have an opening and cross-sectional area of other shapes, such as oblong, elliptical, or even rectangular.

With reference to FIG. 12, an alternative embodiment of a gas delivery device 101 of the present invention being worn by a patient 102 is illustrated. The oxygen delivery device 101 includes a substantially U-shaped tubular nasal cavity component 103 that may be non-flexible or flexible, and may be inserted into either nostril of the patient 102 to deliver gas to the patient. The substantially U-shaped nasal cavity component 103 is preferably constructed from formable or memory material. At juncture 107, the substantially U-shaped nasal cavity component 103 is connected to and in fluid communication with the tubular guidance-stabilization system 108. A stabilization patch 118 is used to secure the tubular guidance-stabilization system 108 at the tip of the patient's cheek.

With reference to FIG. 12, the gas delivery device 101 includes a one-piece flexible stabilization patch 118 made of flexible, breathable and non-irritating material, with a patient-friendly adhesive located on one-side of the patch. The flexible stabilization patch 118 is preferably breathable, having tiny perforations for the health of the skin and for escape of fluids and heat. The one-piece flexible stabilization patch 118 is depicted as a circular patch, but may be of any shape, such as oblong, elliptical, or rectangular. The one-piece flexible stabilization patch 118 may be about one inch in diameter and may have a peel off protective covering on the adhesive side, on which a medical adhesive or glue is applied. The flexible stabilization patch 118 is used to secure the tubular guidance-stabilization system 108 onto the tip of the patient's cheek bone and behind the lower portion of the patient's ear proximate the mastoid tip, where there is no hair and little oil. For instance, after removing the peel off protective covering from the adhesive side of the stabilization patch 118, a medical provider will first position the tubular guidance-stabilization system 108 at the tip of the cheek bone as described herein and then cover the portion of the guidance-stabilization system 108 on the tip of the cheek bone with the adhesive side of the patch and firmly press the remainder of the exposed patch onto the patient's skin.

Figure 13:
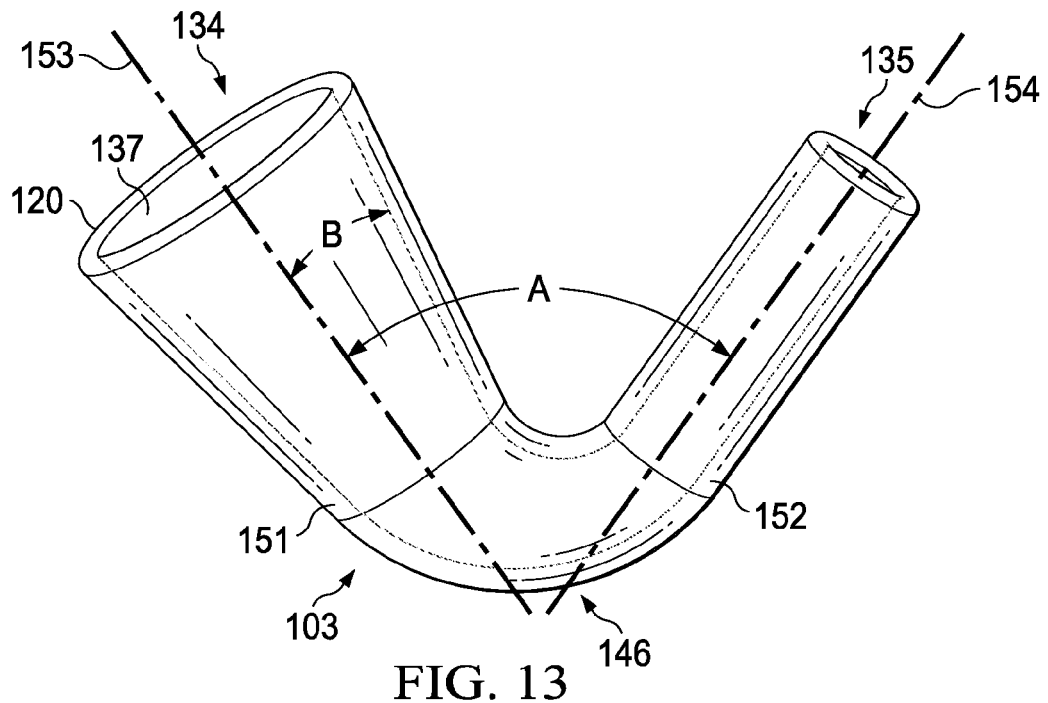
FIG. 13 is a perspective view of a U-shaped tubular nasal cavity component of the present invention.
Figure 17:
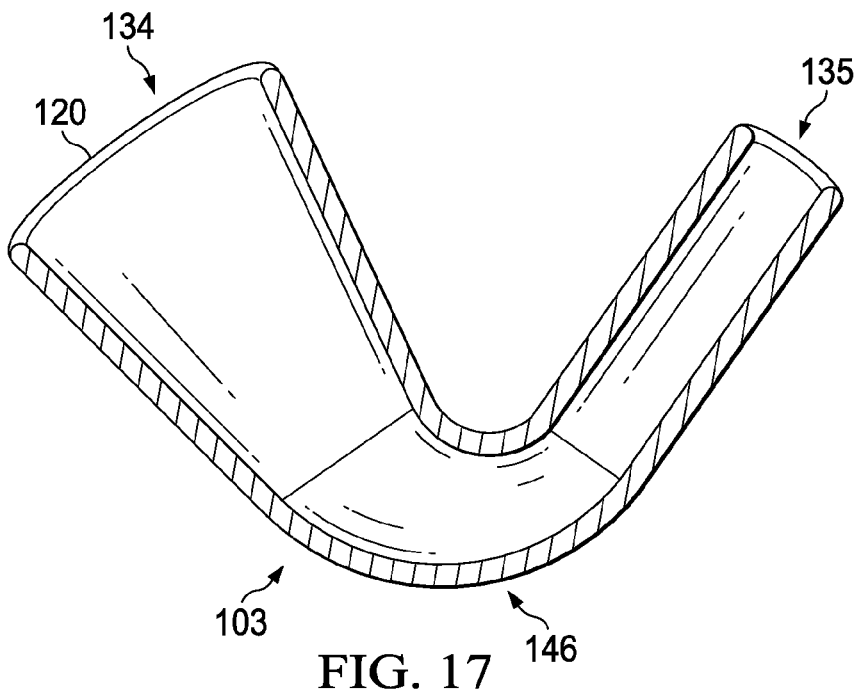
FIG. 17 is a cross-sectional view of a U-shaped tubular nasal cavity component of the present invention.
Figure 18:
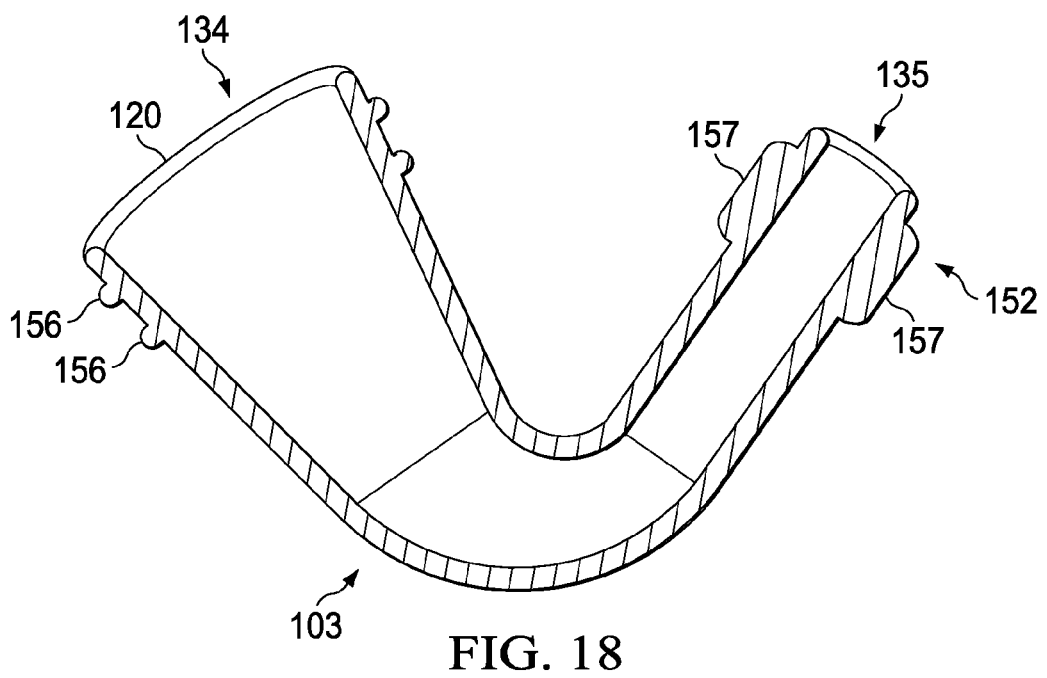
FIG. 18 is a cross-sectional view of a U-shaped tubular nasal cavity component of the present invention, with external ribs and a external gripping members.

When the gas delivery device 101 is in use, the substantially U-shaped nasal cavity component 103 has a first end 134 that fits inside the patient's nostril and a second end 135 exterior to the nostril. The substantially U-shaped nasal cavity component 103 attaches to and is in fluid communication with a flexible and preferably formable or bendable tubular guidance-stabilization system 108. The tubular guidance-stabilization system 108 then extends upward from the second end 135 of the nasal cavity component 103, to the tip of the patient's cheekbone (where the tubular guidance-stabilization system 108 is secured using a stabilization patch 118), and up and over the patient's ear. The tubular guidance-stabilization system 108 is secured to the tip of the mastoid and then is draped across the neck of the patient to the opposite shoulder, where the tubular guidance-stabilization system 108 is clipped to the patient's clothing or hospital gown. At the end of the tubular guidance-stabilization system 108 is the male side of an adapter for connecting the gas delivery system to an oxygen or gas supply source. With reference to FIG. 13 and FIG. 17, a side view and a cross-sectional view of an alternative embodiment of a nasal cavity component 103 of the present invention are illustrated, respectively. The nasal cavity component 103 has a tubular wall 120 of relatively uniform thickness, a first end 134 that is adapted to fit inside the patient's nostril, a first tubular section 151, a bend portion 146, a second tubular section 152, and a second end 135. The tubular wall 120 surrounds and forms a gas passageway 137. To prevent membrane irritation when the nasal cavity component 103 is inserted into the patient's nostril, the first end 134 will preferably have a curved or rounded ending, as depicted in FIG. 18. Although the first tubular section 151 is approximately the same length of the second tubular section 152, these respective lengths may vary and the bend portion may not be located in the center of the nasal cavity component 103.

In another aspect as shown in FIG. 13 and FIG. 17, the first tubular section 151 of the nasal cavity component 103 will have a funnel shape (frustoconical shape) to create a diverging flow path for the gas, such that, for example, the width and cross-sectional area of the gas passageway 137 in the first tubular section 151 is largest at the opening of the nasal cavity component 103 at first end 134, and the width and cross-sectional area of the gas passageway 137 in the first tubular section 151 is smallest proximate the central portion 145. Accordingly, the funnel shape of the tubular section 151 promotes the retention of the nasal cavity component 103 within the patient's nostril and creates a diverging flow path for gas entering the patient's nostril. The angle of diversion (also referred to as the diversion angle), which is the angle measured between the tubular wall 120 in the first end 134 and the longitudinal axis 154 of the first end, preferably ranges from between three degrees and 30 degrees. The funnel shape (frustoconical shape) of the gas passageway 137 within first tubular section 151 of the tubular nasal cavity component 103 allows a diverging gas flow through such first tubular section 151 such that the oxygen or other gas, to be dispersed into the nasal cavity, flows in all directions instead of in a single, narrow flow path. A diverging flow of gas into the nostril results in less irritation and less dryness and cracking of the inside of the nostril. Furthermore, the funnel shape of the gas passageway 137 within first tubular section 151 of the tubular nasal cavity component 103 prevents or at least inhibits or reduces the risk of backflow or escape of the gas outside the nostril and into the ambient air, which in turn establishes a potentially greater nasal cavity reservoir of gas that is available for the patient's next breath.

In another aspect, an alternative embodiment of the nasal cavity component 103 has a substantially U-shape to promote the stability of the gas delivery device 101. As shown in FIG. 13, the first tubular section 151 extends away from the first end 134 toward the bend portion 146, the second tubular section 152 extends from the bend portion 146 to the second end 135. An angle between the longitudinal axis 153 of the first tubular section 151 and the longitudinal axis 154 of the second tubular section 152 is approximately seventy plus or minus ten degrees (70±10°). Alternatively, the angle between the longitudinal axis 153 of the first tubular section 151 and the longitudinal axis 154 of the second tubular section 152 may range between approximately five degrees (5°) and ninety degrees (90°). Accordingly, when in use by a patient, the tubular nasal cavity component 103 is adapted to extend downward from the patient's nostril, around an outer surface of the patient's nostril, and then in an upward direction toward the patient's eye. In this configuration, the bend in the nasal cavity component 103 prevents the formation of kinks in the gas delivery device that could reduce or restrict the flow of gas and also enhances the placement of tubular nasal cavity component and tubular guidance-stabilization system on the patient's face.

Alternatively, the angle between the longitudinal axis 153 of the first tubular section 151 and the longitudinal axis 154 of the second tubular section 152 within nasal cavity component 103 may range from about zero degrees (0°) and about one hundred eighty degrees (180°) without departing from the spirit of the invention. For instance, when the gas delivery device 101 is in use, should the angle of the first tubular section 151 and the longitudinal axis 154 of the second tubular section 152 within nasal cavity component 103 be approximately zero (as depicted in FIG. 10A and FIG. 10B), then the portion of the tubular guidance-stabilization system 108 extending from the second end 134 of the tubular nasal cavity component 103 would be bent approximately seventy plus or minus ten degrees (70±10°) to allow the tubular guidance-stabilization system 108 to then extend upward to the tip of the patient's cheekbone (where the tubular guidance-stabilization system 108 is secured using a stabilization patch 118), and up and over the patient's ear.

Figure 14:
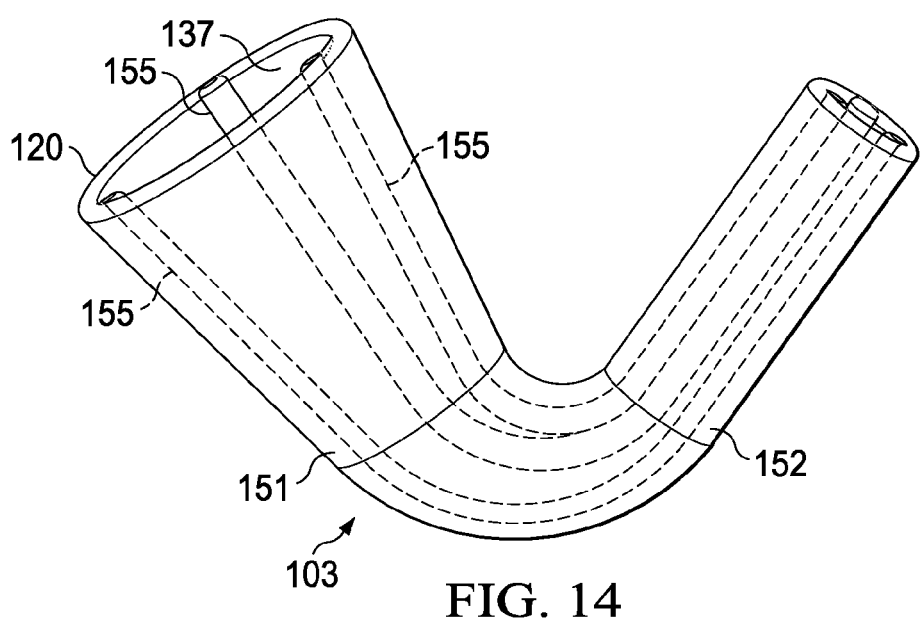
FIG. 14 is a perspective view of a U-shaped tubular nasal cavity component of the present invention, with internal ribs.

Another exemplary embodiment of a nasal cavity component 103 having unique features is depicted in FIG. 14. As shown, one or more internal ribs 155 may be formed during the manufacturing process on the internal side of the tubular wall 120 and extend approximately the entire length of the nasal cavity component 103. The internal ribs 155 provide both axial and radial support to the tubular wall 120, preventing the collapse of the nasal cavity component 103 and the formation of any restrictions that could reduce or restrict the passage of gas through the gas passageway 137. The internal ribs 155 also promote turbulent flow of gas through the nasal cavity component 103 by reducing sharp angled flow conditions therein.

Figure 15:
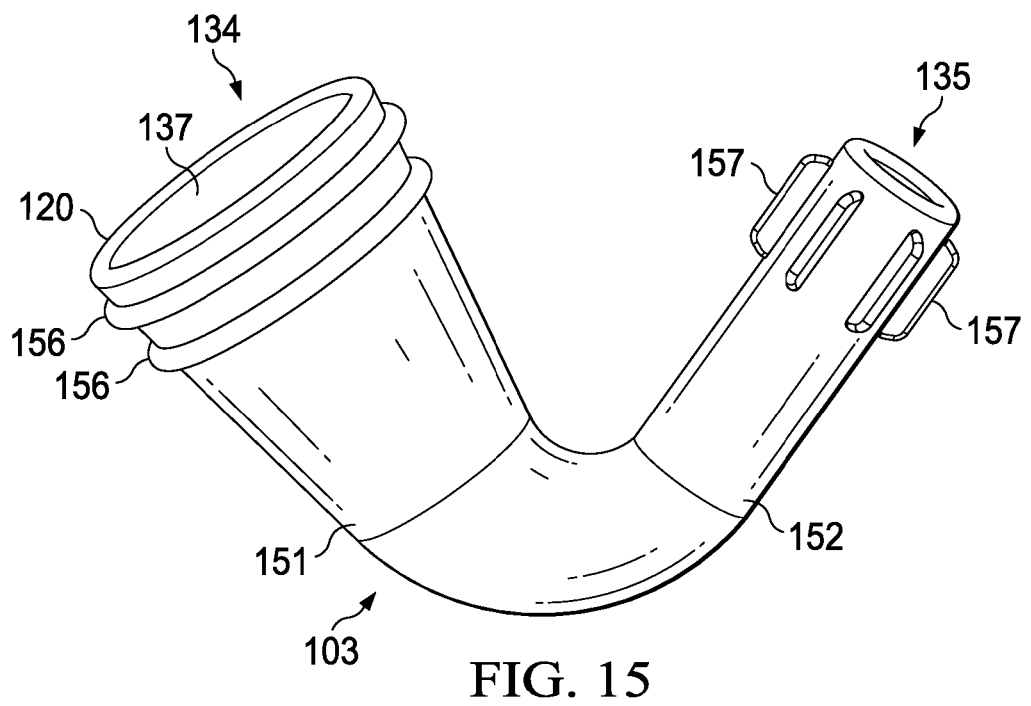
FIG. 15 is a perspective view of a U-shaped tubular nasal cavity component of the present invention, with external ribs and a external gripping members.

Another exemplary embodiment of a nasal cavity component 103 having unique features is depicted in FIG. 15 and FIG. 18. FIG. 15 is a side view of a nasal cavity component 103 and FIG. 18 is a cross-sectional view. The nasal cavity component 103 may include one or more exterior ribs 156 that are formed on the external portion of the tubular wall 120 and positioned proximate to the first end 134 of the nasal cavity component 103. The external ribs 156 are soft and rounded to avoid irritation and discomfort for the patient. The one or more exterior ribs 156 promote strain relief and provide radial support to the first end 134 of the nasal cavity component when inserted within the patient's nostril. Accordingly, the external ribs 156 help secure the nasal cavity component 103 within the patient's nostril. Furthermore, the one or more external ribs 156 provide an additional barrier to reduce the risk of backflow or escape of the gas outside the nostril and into the ambient air, which in turn establishes a potentially greater nasal cavity reservoir of gas that is available for the patient's next breath.

As shown in FIG. 15 and. FIG. 18, the nasal cavity component 103 may include exterior gripping members 157 on the second tubular section 152 near the second end 135 that are useful during assembly or adjustment of the gas delivery device 101, particularly with connecting the nasal cavity component 103 to the tubular guidance-stabilization system 104 and/or making adjustments to the connection.

Figure 16:
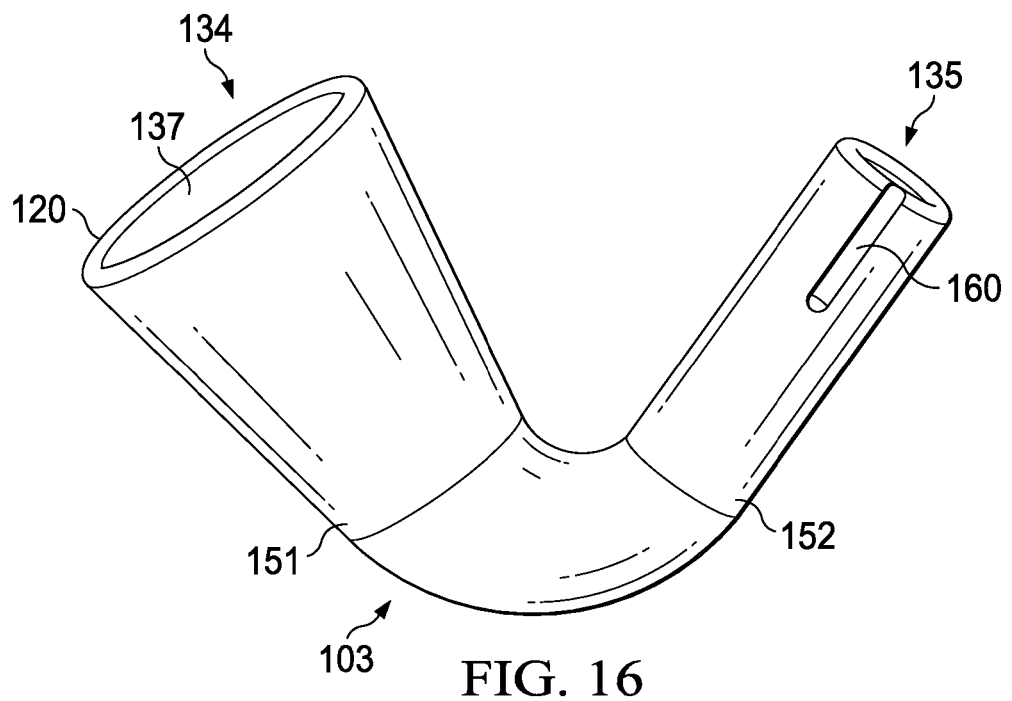
FIG. 16 is a perspective view of a U-shaped tubular nasal cavity component of the present invention, with an external groove.

Another exemplary embodiment of a nasal cavity component 103 having unique features is depicted in FIG. 16, which shows a nasal cavity component 103 having an external slot 160 that promotes alignment of the nasal cavity component 103 with a corresponding tubular guidance-stabilization system 108, during either the initial assembly or subsequent alignment of the gas delivery device. In this configuration, when connecting the nasal cavity component 103 to a tubular guidance-stabilization system 108, the nasal cavity component 103 is considered the male portion of the connection that fits within the female portion of the connection found on the tubular guidance-stabilization system 108. For example, the nasal cavity component 103 shown in FIG. 16 would mate with the tubular guidance-stabilization system 108 shown in either FIG. 21 or FIG. 22, both of which show a cross-sectional view of a tubular guidance-stabilization system 108 having an internal key 170 on the interior of the wall 133 of the tubular guidance-stabilization system 108 for mating with the groove 160 on exterior of the wall 120 of the nasal cavity component 103 of FIG. 16.

Figure 19:
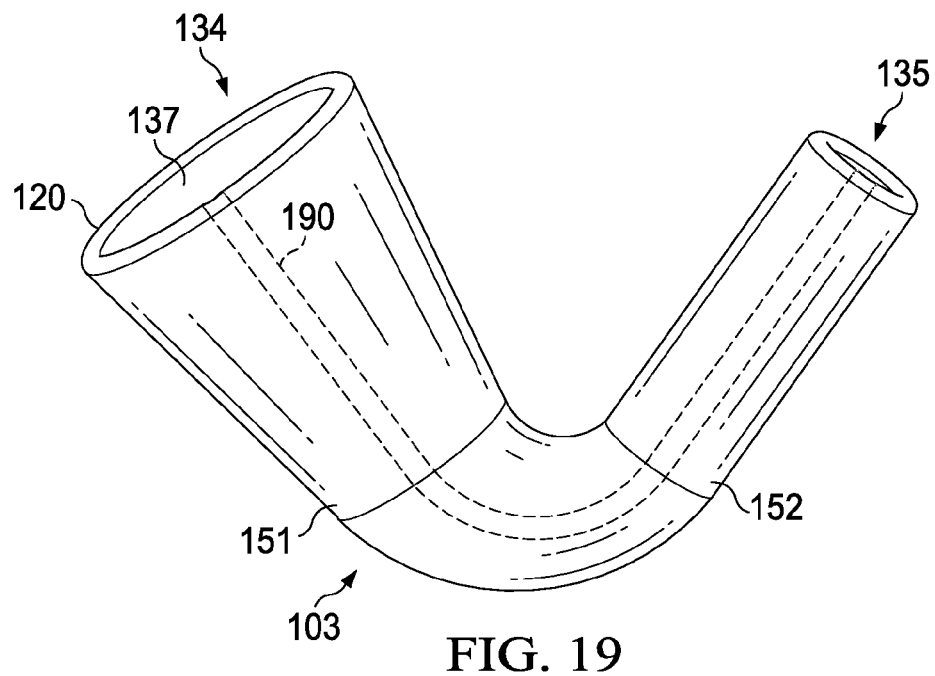
FIG. 19 is a perspective view of a U-shaped tubular nasal cavity component of the present invention, with an internal groove.
Figure 23:
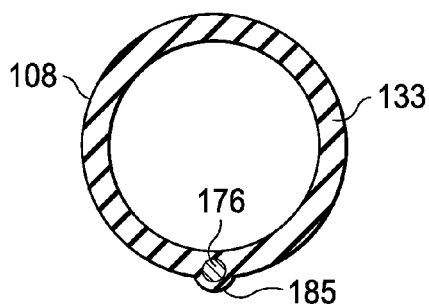
FIG. 23 is a cross-sectional view of tubular guidance-stabilization system of the present invention, showing an external key and a flexible wire within the tubular wall.

Another exemplary embodiment of a nasal cavity component 103 having unique features is depicted in FIG. 19, which shows a nasal cavity component 103 having an internal slot 190 that promotes alignment of the nasal cavity component 103 with a corresponding tubular guidance-stabilization system 108 (not shown in FIG. 19), during either the initial assembly or subsequent alignment of the gas delivery device. In this configuration, when connecting the nasal cavity component 103 to a tubular guidance-stabilization system 108 (not shown in FIG. 19), the nasal cavity component 103 is considered the female portion of the connection into which fits the male portion of the connection found in the tubular guidance-stabilization system 108. For example, the nasal cavity component 103 shown in FIG. 19 would mate as the female connection with the tubular guidance-stabilization system 108 (the male portion of the connection) shown in FIG. 23, which shows a cross-sectional view of a tubular guidance-stabilization system 108 having an external grove or slot 180 on the interior of the wall 130 for mating with the internal groove 190 on the nasal cavity component 103 as shown in FIG. 23.

Figure 24:
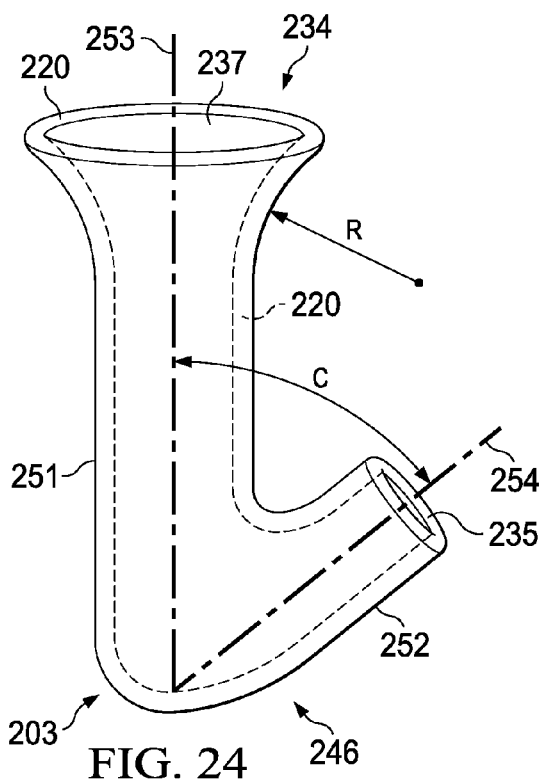
FIG. 24 is a side view of an embodiment of a trumpet-shaped tubular nasal cavity component of the present invention, showing the outward flaring opening at the end that fits into the user's nasal cavity.
Figure 25A:
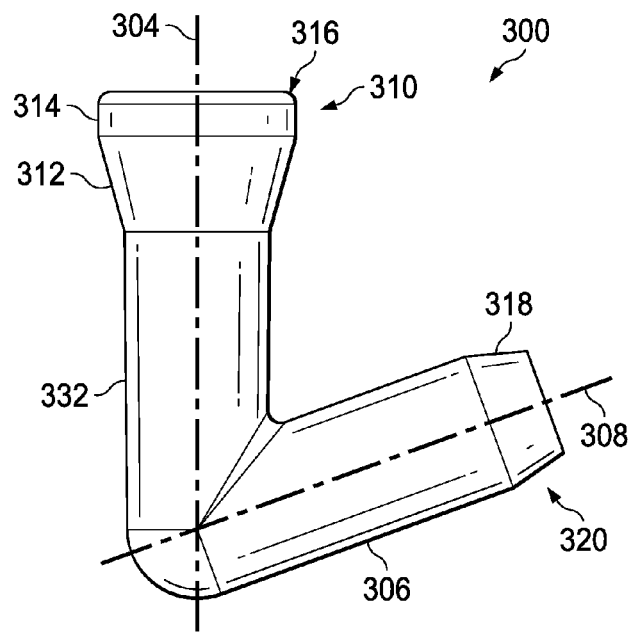
FIG. 25 A is a side view of an exemplary embodiment of a tubular nasal cavity component having two terminal ends: a frusto-conical end, topped with an outward flaring opening, at the end that fits into the user's nasal cavity, and a gas inlet end configured to receive a gas supply tube.
Figure 25B:
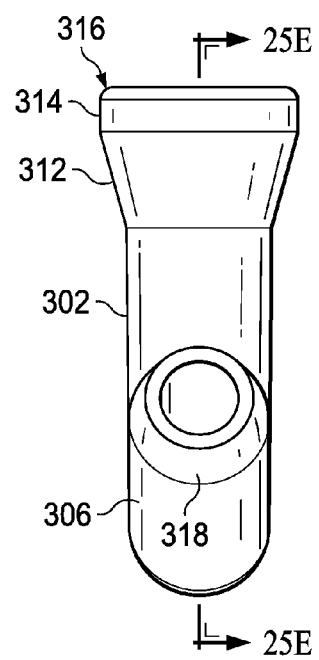
Figure 25C:
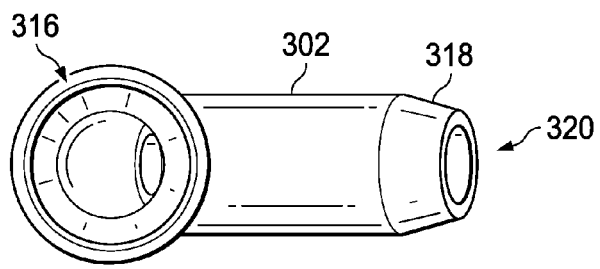
Figure 25D:
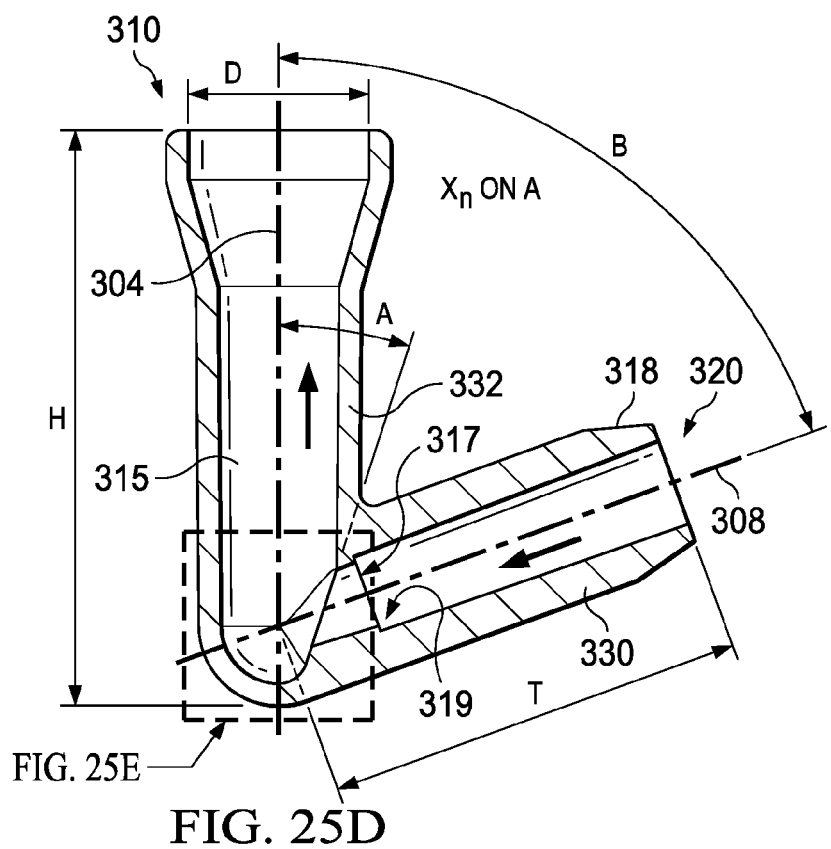
Figure 25E:
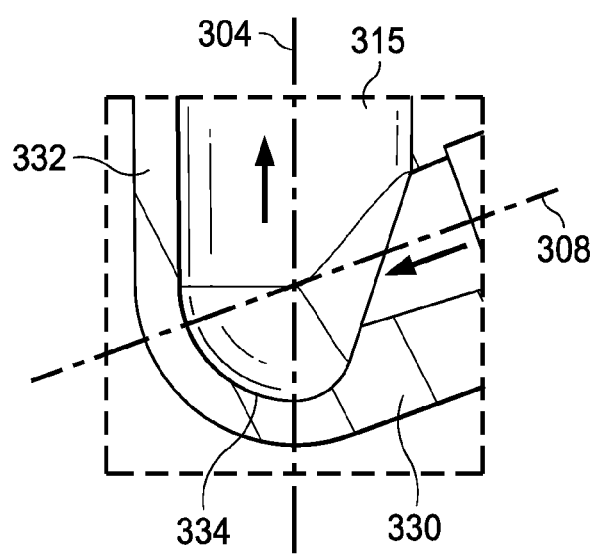

With reference to FIG. 24, a side view of an alternative embodiment of a nasal cavity component 203 of the present invention is illustrated. The nasal cavity component 203 has a tubular wall 220 of relatively uniform thickness, a first end 234 that is adapted to fit inside the patient's nostril, a first tubular section 251, a bend portion 246, a second tubular section 252, and a second end 235. The tubular wall 220 surrounds and forms a gas passageway 237. To prevent membrane irritation when the nasal cavity component 203 is inserted into the patient's nostril, the first end 234 will preferably have a curved or rounded ending, as depicted in FIG. 18. Although the first tubular section 251 is not the same length of the second tubular section 252 as depicted in FIG. 24, these respective lengths may vary and the bend portion may not be located in the center of the nasal cavity component 203.

In another aspect as shown in FIG. 24, the first tubular section 251 of the nasal cavity component 203 will have a trumpet or flared shape, such that the width of the gas passageway 237 in the first tubular section 251 is largest at the opening of the nasal cavity component 203 at first end 234. The trumpet portion at the first end 234 may have an arcuate shape and have, for example, a radius of curvature R, which will vary depending upon other variables, such as the size of the patient's nostril. Accordingly, the trumpet shape of the tubular section 251 promotes the retention of the nasal cavity component 203 within the patient's nostril and creates a diverging flow path for gas entering the patient's nostril. The trumpet shape of the gas passageway 237 within first tubular section 251 of the tubular nasal cavity component 203 allows a diverging gas flow through such first tubular section 251 such that the oxygen or other gas, to be dispersed into the nasal cavity, flows in all directions instead of in a single, narrow flow path. A diverging flow of gas into the nostril results in less irritation and less dryness and cracking of the inside of the nostril. Furthermore, the trumpet shape of the gas passageway 237 within first tubular section 251 of the tubular nasal cavity component 203 prevents or at least inhibits or reduces the risk of backflow or escape of the gas outside the nostril and into the ambient air, which in turn establishes a potentially greater nasal cavity reservoir of gas that is available for the patient's next breath.

In another aspect, an alternative embodiment of the nasal cavity component 203 has a substantially U-shape to promote the stability of the gas delivery device 201. As shown in FIG. 24, the first tubular section 251 extends away from the first end 234 toward the bend portion 246, and the second tubular section 252 extends from the bend portion 246 to the second end 235. An angle between the longitudinal axis 253 of the first tubular section 251 and the longitudinal axis 254 of the second tubular section 252 is approximately seventy plus or minus ten degrees (70±10°). Alternatively, the angle between the longitudinal axis 253 of the first tubular section 251 and the longitudinal axis 254 of the second tubular section 252 may range between approximately five degrees (5°) and ninety degrees (90°). Accordingly, when in use by a patient, the tubular nasal cavity component 203 is adapted to extend downward from the patient's nostril, around an outer surface of the patient's nostril, and then in an upward direction toward the patient's eye. In this configuration, the bend in the nasal cavity component 203 prevents the formation of kinks in the gas delivery device that could reduce or restrict the flow of gas and also enhances the placement of tubular nasal cavity component and tubular guidance-stabilization system on the patient's face.

Alternatively, the angle between the longitudinal axis 253 of the first tubular section 251 and the longitudinal axis 254 of the second tubular section 252 within nasal cavity component 203 may range from about zero degrees (0°) and about one hundred eighty degrees (180°) without departing from the spirit of the invention. For instance, when the gas delivery device 201 is in use, should the angle of the first tubular section 251 and the longitudinal axis 254 of the second tubular section 252 within nasal cavity component 203 be approximately zero (as depicted in FIG. 10A and FIG. 10B), then the portion of the corresponding tubular guidance-stabilization system 108 (illustrated in FIG. 12) extending from the second end 134 of the tubular nasal cavity component 103 would be bent approximately seventy plus or minus ten degrees (70±10°) to allow the tubular guidance-stabilization system 108 to then extends upward to the tip of the patient's cheekbone (where the tubular guidance-stabilization system 108 is secured using a stabilization patch 118), and up and over the patient's ear.

As illustrated in FIGS. 10A, 10B, 13 through 19, and 24, the opening and the cross-sectional area of the gas passageway (37, 137, and 237) at the first end (i.e., 34, 134, and 234) of the substantially U-shaped tubular nasal cavity component (46, 103 and 203) is depicted as being circular. However, it is understood that the cross-sectional area for flow of the tubular nasal cavity component, and that each such opening, may be circular, oblong, or elliptical, or have other shapes and still accomplish the goals of the subject invention.

Figure 20:
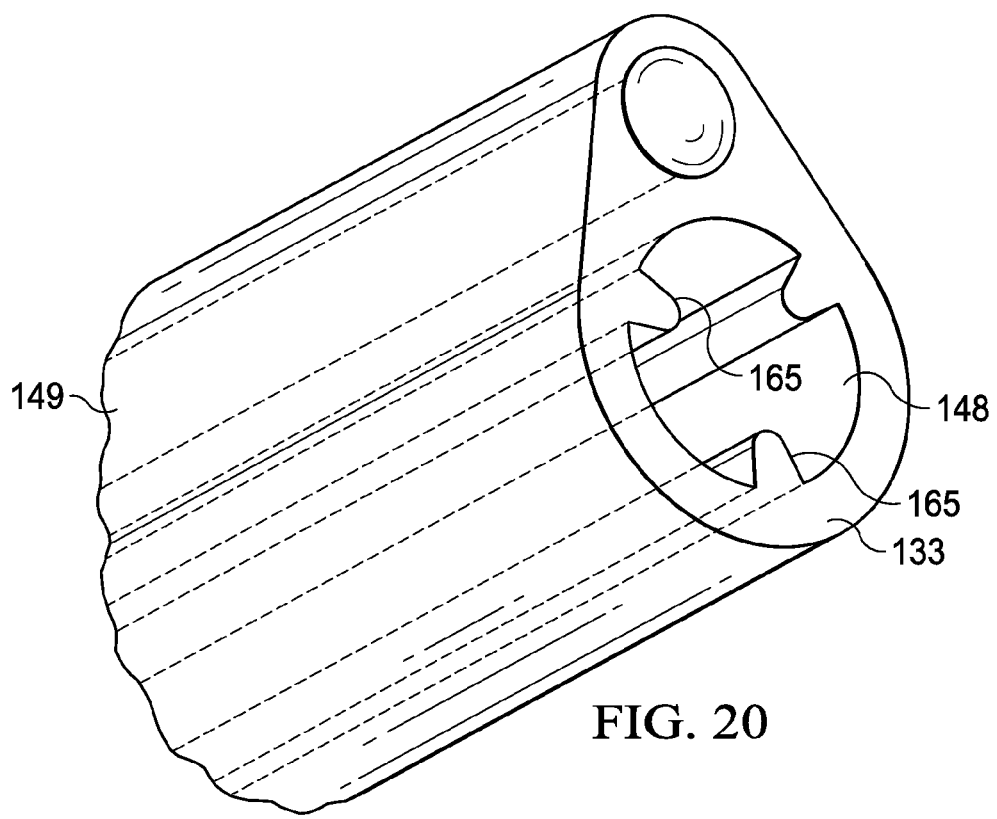
FIG. 20 is a is a perspective of a first section of a tubular guidance-stabilization system of the present invention, showing internal ribs extending longitudinally within the tubular wall.

With reference to FIG. 20, an alternative embodiment of a tubular guidance-stabilization system 108 is shown that includes a tubular wall 133 and a gas passageway 148 formed in the tubular wall. A wire (not shown) may be inserted within channel 149, which extends in a longitudinal direction within the tubular wall 133. Alternatively, the wire is embedded in the tubular wall 133 during the manufacturing process, which may involve injection molding. The tubular wall 133 may also include one or more internal ribs 165 that extend along the tubular wall 133 to provide both axial and radial support to the tubular wall 133, preventing the collapse of the tubular guidance-stabilization system 108 and the formation of any restrictions that could reduce or restrict the passage of gas through the gas passageway 148.

Figure 21:
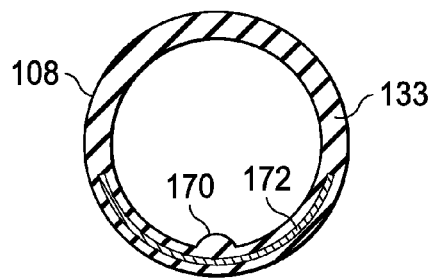
FIG. 21 is a cross-sectional view of tubular guidance-stabilization system of the present invention, showing an internal key and a flexible metal band within the tubular wall.
Figure 22:
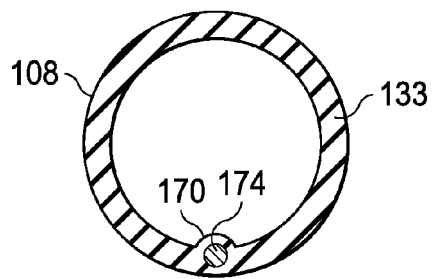
FIG. 22 is a cross-sectional view of tubular guidance-stabilization system of the present invention, showing an internal key and a flexible wire within the tubular wall.

As discussed herein, FIGS. 21, 22 and 23 are cross-sectional views of an alternative tubular guidance-stabilization system 108 of the present invention. The guidance-stabilization system 108 may have internal or external keys to properly align, during assembly or adjustment of the gas delivery device, the guidance-stabilization system 108 with the nasal cavity component 103 having a corresponding external or internal groove or slot.

As shown in FIG. 21, the tubular guidance-stabilization system 108 includes a tubular wall 133 and an internal key 170 that extends inwardly in a radial direction from the wall and extends along at least a portion of the tubular wall 133 in a longitudinal direction starting from the end of the tubular guidance-stabilization system 108 that is connected to, in fluid connection with, and mates with the tubular nasal cavity component 103 (not shown in FIG. 21). The tubular guidance-stabilization system 108 also includes a flexible metal or composite band 172 that extends in a longitudinal direction within the wall 133 from the end of the tubular guidance-stabilization system 108 that is connected to, in fluid connection with, and mates with the tubular nasal cavity component 103 (not shown in FIG. 21) and terminates at a position approximately one inch below where the tubular guidance-stabilization system is secured behind the patient's ear as described herein. In one exemplary embodiment, the band 172 and the internal key 170 are both positioned at the 6 o'clock position as shown in FIG. 21. The key 170 is used for alignment of the tubular guidance-stabilization system 108 with the nasal cavity component 103, which has a mating groove or slot 180 in (as shown in FIG. 16). In this configuration, the end of the tubular guidance-stabilization system 108 acts as the female portion of the connection and the corresponding second end 135 of the nasal cavity component 103 (as depicted in FIG. 19) acts as the male portion of the connection.

As shown in FIG. 22, the tubular guidance-stabilization system 108 includes a tubular wall 133 and an internal key 170 that extends inwardly in a radial direction from the wall and extends along at least a portion of the tubular wall 133 in a longitudinal direction starting from the end of the tubular guidance-stabilization system 108 that is connected to, in fluid connection with, and mates with the tubular nasal cavity component 103 (not shown in FIG. 22). The tubular guidance-stabilization system 108 also includes a flexible wire 174 that extends in a longitudinal direction within the tubular wall 133 from the end of the tubular guidance-stabilization system 108 that is connected to, in fluid connection with, and mates with the tubular nasal cavity component 103 (not shown in FIG. 22) and terminates at a position approximately one inch below where the tubular guidance-stabilization system is secured behind the patient's ear as described herein. In one exemplary embodiment, the wire 174 and the internal key 170 are both positioned at the 6 o'clock position as depicted in FIG. 22. In this configuration, the end of the tubular guidance-stabilization system 108 acts as the female portion of the connection and the second end 135 of the nasal cavity component 103 (as depicted in FIG. 16) acts as the male portion of the connection.

As shown in FIG. 23, the tubular guidance-stabilization system 108 includes a tubular wall 133 and an external key 185 that extends inwardly in a radial direction from the wall and extends along at least a portion of the tubular wall 133 in a longitudinal direction starting from the end of the tubular guidance-stabilization system 108 that is connected to, in fluid connection with, and mates with the tubular nasal cavity component 103 (not shown in FIG. 23). The tubular guidance-stabilization system 108 also includes a flexible wire 176 that extends in a longitudinal direction within the tubular wall 133 from the end of the tubular guidance-stabilization system 108 that is connected to, in fluid connection with, and mates with the tubular nasal cavity component 103 (not shown in FIG. 23) and terminates at a position approximately one inch below where the tubular guidance-stabilization system is secured behind the patient's ear as described herein. In one exemplary embodiment, the wire 176 and the external key 185 are both positioned at the 6 o'clock position as depicted in FIG. 23. The external key 185 is used for alignment of the tubular guidance-stabilization system 108 with the nasal cavity component 103, which has a mating groove or slot 180 in (as shown in FIG. 19). In this configuration, end of the tubular guidance-stabilization system 108 acts as the male portion of the connection and the second end 135 the nasal cavity component 103 (as depicted in FIG. 19) acts as the female portion of the connection.

In a further exemplary embodiment of a tubular nasal cavity component (cannula) 300, illustrated schematically in FIGS. 25A-D, the cannula has two terminal ends: a gas inlet end 320 and a gas outlet end 310. A single gas flow path 315 extends from the gas inlet end 310 to the gas outlet end 320, as seen more clearly in FIG. 25D. The arrow indicates the direction of supplied gas flow in normal use. The cannula 300 is configured for insertion of the gas outlet end 310 into a nostril of a patient and is adapted to maintain the outlet end 310 in an inserted position without adhesive. The cannula 300 includes: a first portion 332 (depicted vertical in FIGS. 25 A, D and F) having a length H and a first longitudinal axis 304 along the single gas flow path 315. The gas outlet end (proximal end as depicted) 310 of the first portion is flared outward, as detailed further here below, and is configured for insertion into a nostril of a patient. A second portion 330 of the cannula 300, depicted as extending from a distal end of the first portion at an acute angle, has a second longitudinal axis 308. The second portion 330 includes the gas inlet end 320 that is configured to facilitate coupling to a gas supply tubing to convey gas to the cannula 300 from a gas supply. The distal end of the second portion 330 intersects the distal end of the first portion 332 in a bend or "elbow" portion, such that the second longitudinal axis 308 and the first longitudinal axis 304 intersect at an acute angle B. Optionally, B ranges between about 60 and about 80°.

As illustrated, the exemplary embodiment of FIG. 25 A-D has a substantially frusto-conical outward flaring tip 312 crowned with a substantially cylindrical tip 314. The cylindrical tip, preferably for user comfort but not necessarily, includes a rounded curvature 316 of the perimeter at the extremity thereof to present a smooth surface without sharp edges that interfaces with the inner portion of the user's nostril.

In addition, optionally an inner surface 334 of the distal end of the first portion 332 is smoothly curved, as seen in side cross section in FIG. 25 E, up to an intersection with an inner surface of the distal end of the second portion 330. The smoothly rounded curvature 334 may terminate at a tangent to the inner surface of the distal end of the second portion 330 at an angle A which may range from about 16 to about 20 degrees to the first longitudinal axis 304.

Preferably, the cannula is made of a soft and pliable medical grade plastic, as also detailed elsewhere herein with reference to other embodiments. The terms "substantially frusto-conical" and "substantially cylindrical" as these relate to the tip of a cannula are intended to take into account that materials and methods of manufacture that may result in shapes that may deviate slightly from the literal geometry. To the extent that the term "substantially" may be objected to, it should nonetheless be understood that as a practical matter the terms "frusto-conical" and "cylindrical" are not exact as a matter of practical manufacture.

It is understood that fluid dynamics play a significant role in the distribution and flow patterns of gas delivered via the cannula 300. In turn, the geometry of the cannula, in terms of relative dimensions of its features affects the nature of the fluid dynamics. As a consequence, the exemplary cannula 300 tip inner diameter D and length H of the first portion are each preferably sized such that gas exits from the nasal cannula in a vortex flow pattern when the nasal cannula is in use. Moreover, it has been found that when the gas includes oxygen, user oxygen intake is improved when using the exemplary cannula 300. It is theorized, without being bound, that the vortex flow increases oxygen intake by the user, as compared to using a nasal cannula without a vortex flow In the exemplary cannula 300, preferably, but not necessarily, the length H of the first portion is about 3 to about 2 times an internal diameter D of the proximal end. In addition, the length T of the second portion is preferably, but not necessarily, about 1.7 to about 1.2 times an internal diameter D of the proximal end.

FIG. 26 is a cross sectional view through an exemplary embodiment of a gas delivery tube 350. The tube has a sidewall that can be regarded as a thin sidewall portion 352 and a thick sidewall portion 354, that together surround a cross sectional area for gas flow 358 having a shape of a portion of a circle. A flexible, electricity-conducting conduit such as cable 356, capable of transmitting electricity and/or signals from a sensor, is embedded (or otherwise located in a lumen) in the thick sidewall portion 354. The cable 356 may be metallic wire or electrical conducting polymer. In a preferred embodiment, the cable has the ductility and resilience to maintain the gas delivery tube in a desired shape or position when it is deployed as part of a gas delivery system.

FIG. 27 is a cross sectional view through another exemplary embodiment of a gas delivery tube 360. The tube has a sidewall that can be regarded as a thin sidewall portion 362 and a thick sidewall portion 364, that together surround a cross sectional area for gas flow 368 having a shape of a portion of a circle. In this embodiment there are two flexible, electricity-conducting conduits such as cables 366, 366 (although clearly more may be added, as desired), capable of transmitting electricity and/or signals from a sensor, embedded in the thick sidewall portion 364. The cables 366, 366 may each be metallic wire or electrical conducting polymer. In a preferred embodiment, at least one of the cables (or the cables together) has the ductility and resilience to maintain the gas delivery tube in a desired shape or position when it is deployed as part of a gas delivery system.

FIG. 28 illustrates a yet further cross sectional view of an exemplary embodiment of a gas supply tube, 370. The tube 370 includes an internal septum 374 along its length, that may be extruded along with the gas tube, and that extends across from one side of the tube wall 372 to the other. The upper space 378 may be used for gas flow. The lower space 375 may be used for at least one cable 376. The cables 376 may each be metallic wire or electrical conducting polymer. In a preferred embodiment, at least one of the cables (or the cables taken together) has the ductility and resilience to maintain the gas delivery tube in a desired shape or position when it is deployed as part of a gas delivery system, FIG. 25F illustrates an exemplary embodiment of a cannula 300 with a gas tube 400 coupled to it. The gas delivery tube 400 extends into the cannula 300 from the tapered gas inlet end 318 until it encounters a mechanical stop 317, 319 (in the inner walls of the second portion 330) and is held firmly in place, either by friction or an exterior locking mechanism (not shown), or both. The tip of the gas delivery tube 400 has at least one electrically conducting conduit 410 extending from it, to at least one sensor 420. Thus, parameters detected by the sensor may be transmitted along the conduit 410 to receiving electronics for analysis, display, alarm, and such other functions as may be useful. Of course, the sensor may also be configured with a transmitter to send detected data wirelessly, for example via Bluetooth, or other protocol. The sensor(s) may be selected to monitor a variety of parameters, such as temperature, oxygen, water (vapor), carbon dioxide, nitrogen, ammonia, nitrous oxide, nitric oxides, and other therapeutic and exhalation materials.

It is to be understood that while a preferred embodiment of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

The invention claimed is:

1. A system for delivery of a gas to a patient, the system comprising:
    a single tubular nasal cavity component comprising only two terminal ends, including one end for gas inlet and one end for gas outlet with a single gas flow path extending from the gas inlet end to the gas outlet ends, the tubular nasal component configured for insertion into a nostril of a patient and adapted to maintain an inserted position, the single tubular nasal cavity component comprising:
        a first portion having a length H and a first longitudinal axis along the single gas flow path, and a single proximal end, the proximal end configured for insertion into a nostril of a patient, the proximal end flaring outward to increasingly wider dimensions as it extends toward the gas outlet end, and
        a second portion having a length T and a second longitudinal axis along the single gas flow path, the second portion having a gas inlet end configured to receive gas from a gas supply, a distal end of the second portion intersecting a distal end of the first portion in a bend portion of the single gas flow path, such that the second longitudinal axis and the first longitudinal axis intersect at an angle of between about 60 and about 80°;
        wherein a ratio of H/T ranges from about 2.5 to about 1.18.

2. The system for delivery of a gas to a patient of claim 1, wherein the proximal end of the first portion comprises a substantially frusto-conical outward flaring proximal end.

3. The system for delivery of a gas to a patient of claim 2, further comprising gas supply tubing attached to the gas inlet end of the second portion, the gas supply tubing having at least one flexible wire inserted along a length thereof, the gas supply tubing having a length to extend from the gas inlet end of the second portion end of the nasal cavity component, across the cheek of the user, and over the ear of the user such that during use, the at least one flexible wire maintains a configuration of the gas supply tubing for supporting secure placement of the nasal cavity component in a nostril of a user, and gas flows from the gas supply tubing to the single gas flow path in the nasal cavity component.

4. The system for delivery of a gas to a patient of claim 3, wherein the system includes at least one sensor in proximity to or in the nasal cavity component, and the at least one flexible wire comprises an electricity conducting conduit in communication with the at least one sensor.

5. The system for delivery of a gas to a patient of claim 4, wherein the at least one electricity conducting conduit is comprised of metal or an electricity conducting polymer.

6. The system for delivery of a gas to a patient of claim 3, wherein the system includes at least one sensor in proximity to or in the nasal cavity component, and the at least one sensor transmits sensed data wirelessly.

7. The system for delivery of a gas to a patient of claim 3, wherein an inner surface of the distal end of the first portion is smoothly curved, as seen in side cross section, up to an intersection with an inner surface of the distal end of the second portion.

8. The system for delivery of a gas to a patient of claim 7, wherein the smoothly rounded curvature terminates at a tangent to the inner surface of the distal end of the second portion at an angle of about 16 to about 20 degrees to the first longitudinal axis.

9. The system for delivery of a gas to a patient of claim 3, wherein a length of the first portion is about 3 to about 2 times an internal diameter D of the gas outlet end.

10. The system for delivery of a gas to a patient of claim 3, wherein a length of the second portion is about 1.7 to about 1.2 times an internal diameter D of the gas outlet end.

11. The system for delivery of a gas to a patient of claim 10, wherein a length of the second portion is about 1.7 to about 1.2 times an internal diameter D of the gas outlet end.

12. The system for delivery of a gas to a patient of claim 2, wherein the proximal end and a length of the first portion are each configured such that air flows around the nasal cannula when the nasal cannula is inserted in a nostril of a user.

13. The system for delivery of a gas to a patient of claim 2, wherein the proximal end and a length of the first portion are each configured such that gas exits from the nasal cannula in a vortex flow pattern when the nasal cannula is in use.

14. The system for delivery of a gas to a patient of claim 13, wherein when the gas includes oxygen, the vortex flow increases oxygen intake by the user, as compared to using a nasal cannula without a vortex flow.

15. The system for delivery of a gas to a patient of claim 2, wherein the flared frusto-conical proximal end is crowned with a substantially cylindrical tip.

16. The system for delivery of a gas to a patient of claim 15, wherein the substantially cylindrical tip includes a rounded curvature at an upper extremity thereof.

17. The system for delivery of a gas to a patient of claim 1, wherein an inner surface of the distal end of the first portion is smoothly curved, as seen in side cross section, up to an intersection with an inner surface of the distal end of the second portion.

18. The system for delivery of a gas to a patient of claim 17, wherein the smoothly rounded curvature terminates at a tangent to the inner surface of the distal end of the second portion at an angle of about 16 to about 20 degrees to the first longitudinal axis.

19. The system for delivery of a gas to a patient of claim 1, wherein a length of the first portion is about 3 to about 2 times an internal diameter D of the gas outlet end.

20. The system for delivery of a gas to a patient of claim 1, wherein a length of the second portion is about 1.7 to about 1.2 times an internal diameter D of the gas outlet end.

21. A system for delivery of a gas to a patient, the system comprising:
    a single tubular nasal cavity component comprising only two terminal ends, including one end for gas inlet and one end for gas outlet with a single gas flow path extending from the gas inlet end to the gas outlet end, the tubular nasal component configured for insertion into a nostril of a patient and adapted to maintain an inserted position therein, the single tubular nasal cavity component comprising:
        a first portion having a length H and a first longitudinal axis along the single gas flow path, a proximal end of the first portion sized and configured for insertion into a nostril of a patient, the proximal end comprising a frusto-conical shape flaring outward to wider dimensions as it extends toward the gas outlet end, and having a cylindrical crown at the gas outlet end, and
        a second portion having a length T and a second longitudinal axis, the second portion having a gas inlet end to receive gas from a gas supply, a distal end of the second portion intersecting a distal end of the first portion in a bend portion of the single gas flow path, such that the second longitudinal axis and the first longitudinal axis intersect at an acute angle;
    wherein a ratio of H/T ranges from 2.5 to 1.18.

22. The system for delivery of a gas to a patient of claim 21, wherein an inner surface of the distal end of the first portion is smoothly curved, as seen in side cross section, up to an intersection with an inner surface of the distal end of the second portion.

23. The system for delivery of a gas to a patient of claim 22, wherein the smoothly rounded curvature terminates at a tangent to the inner surface of the distal end of the second portion at an angle of about 16 to about 20 degrees to the first longitudinal axis.

24. The system for delivery of a gas to a patient of claim 21, wherein a length of the first portion is about 2 to about 3 times an internal diameter D of the gas outlet end.

25. The system for delivery of a gas to a patient of claim 21, wherein the first and second longitudinal axes intersect at an angle of from about 60 to about 80°.

26. A system for delivery of a gas to a patient, the system comprising:
    a single tubular nasal cavity component comprising only two terminal ends, including one end for gas inlet and one end for gas outlet with a single gas flow path extending from the gas inlet end to the gas outlet end, the tubular nasal component configured for insertion into a nostril of a patient and adapted to maintain an inserted position, the single tubular nasal cavity component comprising:
        a first portion having a first longitudinal axis along the single gas flow path, and a single substantially frusto-conical proximal end, the proximal end configured for insertion into a nostril of a patient, the proximal end flaring outward to increasingly wider dimensions as it extends toward the gas outlet end; and a second portion having a second longitudinal axis along the single gas flow path, the second portion having a gas inlet end configured to receive gas from a gas supply, a distal end of the second portion intersecting a distal end of the first portion in a bend portion of the single gas flow path, such that the second longitudinal axis and the first longitudinal axis intersect at an angle of between about 60 and about 80°;

wherein a length of the first portion is about 3 to about 2 times an internal diameter D of the gas outlet end, and a length of the second portion is about 1.7 to about 1.2 times an internal diameter D of the gas outlet end.

27. The system for delivery of a gas to a patient of claim 26, wherein the proximal end is crowned with a substantially cylindrical tip.

* * * * *